United States Patent
Ali et al.

(10) Patent No.: US 7,996,243 B1
(45) Date of Patent: Aug. 9, 2011

(54) METHOD AND SYSTEM FOR CALCULATING AN ALIGNMENT DATE FOR PRESCRIPTIONS

(75) Inventors: Syed Y. Ali, Chicago, IL (US); Greg Pankow, Morton Grove, IL (US); Amy C. Biesenthal, Buffalo Grove, IL (US); Deivasigamani Karichianna Gounder, Wheeling, IL (US); Sean McGonagle, Buffalo Grove, IL (US); Victor Lee, Lake Forest, IL (US); Rishi Khullar, Deerfield, IL (US); Christina P. Marotta, Chicago, IL (US)

(73) Assignee: Walgreen Co., Deerfield, IL (US)

( * ) Notice: Subject to any disclaimer, the term of this patent is extended or adjusted under 35 U.S.C. 154(b) by 523 days.

(21) Appl. No.: 12/276,053

(22) Filed: Nov. 21, 2008

(51) Int. Cl.
*G06Q 10/00* (2006.01)
(52) U.S. Cl. .......................................................... 705/2
(58) Field of Classification Search ................... 705/2, 3
See application file for complete search history.

(56) References Cited

U.S. PATENT DOCUMENTS

| | | | | |
|---|---|---|---|---|
| 5,845,255 | A * | 12/1998 | Mayaud ............................ | 705/3 |
| 7,426,476 | B2 * | 9/2008 | Munoz et al. ..................... | 705/3 |
| 7,856,363 | B2 | 12/2010 | Palazzolo et al. | |
| 2002/0032582 | A1 * | 3/2002 | Feeney et al. ..................... | 705/2 |
| 2008/0308445 | A1 | 12/2008 | Dolak | |
| 2009/0030719 | A1 | 1/2009 | Nadas et al. | |
| 2009/0030720 | A1 | 1/2009 | Nadas et al. | |
| 2009/0030725 | A1 | 1/2009 | Nadas et al. | |
| 2009/0043608 | A1 | 2/2009 | Nadas et al. | |
| 2009/0043610 | A1 | 2/2009 | Nadas et al. | |
| 2009/0043611 | A1 | 2/2009 | Nadas et al. | |

OTHER PUBLICATIONS

Salganie, M. William, "A Pill on Time Seems to Help the Bottom Line", Sep. 9, 2002, The Baltimore Sun, Business.
Office action for U.S. Appl. No. 11/781,926 dated Feb. 11, 2011.
U.S. Appl. No. 12/942,779 filed Nov. 9, 2010 entitled, "Method and System for Aligning a Plurality of Refill Dates for Prescriptions Associated with a Plurality of Customers."
U.S. Appl. No. 12/694,968 filed Jan. 27, 2010 entitled "Method and System for Calculating an Alignment Date for Prescriptions."
U.S. Appl. No. 12/694,974 filed Jan. 27, 2010 entitled "Method and System for Charging Customers for Prescription Alignment."
U.S. Appl. No. 12/900,728 filed Oct. 8, 2010 entitled "Method and System for Delivering to a Customer a Plurality of Prescriptions Having Aligned Refill Dates."
U.S. Appl. No. 11/781,938, filed Jul. 23, 2007, on behalf of Nadas et al., entitled "Method and System for Delivering to a Customer a Plurality of Prescriptions Having Aligned Refill Dates".
U.S. Appl. No. 11/926,817, filed Oct. 29, 2007, on behalf of Lewis, entitled "Method of Increasing Compliance of a Medication Within a Multi-Dose Blister Pack".
U.S. Appl. No. 12/275,891, filed Nov. 21, 2008, on behalf of Pankow et al., entitled "Method and System for Enrolling in a Medication Compliance Packaging Program".

(Continued)

*Primary Examiner* — Gerald J. O'Connor
*Assistant Examiner* — Edward Winston, III
(74) *Attorney, Agent, or Firm* — Francis C. Kowalik, Walgreen Co.

(57) ABSTRACT

A system and method facilitate alignment of refill dates associated with a plurality of prescriptions, such that each of the plurality of prescriptions requires a refill on the same date, thus limiting the number of occasions on which a customer must visit the pharmacy to retrieve refills of the aligned prescriptions, and increasing the likelihood that the customer will comply with the prescribed medication regimen. The system and method facilitate the alignment of the refill dates while complying with one or more rules governing the adjudication of the prescriptions.

36 Claims, 9 Drawing Sheets

OTHER PUBLICATIONS

U.S. Appl. No. 12/276,073, filed Nov. 21, 2008, on behalf of Ali et al., entitled "Method and System for Aligning Prescriptions to a User-Selected Date".

U.S. Appl. No. 60/963,871, filed Aug. 31, 2006, on behalf of Nadas et al., entitled "Comprehensive Medication Management System".

* cited by examiner

METHOD AND SYSTEM FOR CALCULATING AN ALIGNMENT DATE FOR PRESCRIPTIONS

FIELD OF THE INVENTION

The present disclosure generally relates to a process for aligning fill dates for a plurality of prescription medications.

BACKGROUND

Generally, customers fill prescription medication orders (hereinafter, "prescriptions") on the day on which they are prescribed, or shortly thereafter. Because prescriptions may be written and filled at different times, and for different quantities of medication, it is common for a customer with multiple prescriptions to run out of the prescribed medications at varying times. Ordering and picking up refills for the various prescriptions at different times may be an inconvenience for a customer, for example, where the store location is not convenient, where a customer depends on others to pick up the prescription, or where a customer's schedule does not coincide with the pharmacy schedule. Additionally, many customers may be unable to remember multiple dates on which they must order or pick up prescription refills. This may affect the customer's health, as it may lead to missed or skipped doses of medication. Mail order and call-center-based services mitigate or alleviate some of these problems, but it is still incumbent on customers to remember to order the refills of their prescriptions. Various rules promulgated by third-parties, such as insurance companies or regulatory agencies, place restrictions on the periods during which a pharmacy may refill prescriptions or on the amount of medication that the pharmacy may dispense in a given time period, further complicating the situation.

SUMMARY OF THE DISCLOSURE

A disclosed method quickly and efficiently generates a prescription alignment plan, thereby enabling a system implementing the method to align the refill dates of a plurality of prescriptions associated with a customer, which alignment decreases the burden on the customer of remembering to refill each prescription, and decreases the frequency with which the customer must receive or pick up the various refilled prescriptions.

The disclosed method complies with applicable regulations, the rules of any third-party payors, and the individual prescriptions associated with the customer. A system implementing the method receives a selection of a plurality of eligible prescriptions to be aligned. For each selected prescription, the system determines how much of the prescribed medication the customer has or should have remaining. If adjudication rules apply to the prescription and/or the customer, the system also determines, for each prescription, a next adjudication date. The system determines an alignment adjudication date by selecting the latest of the next adjudication dates and, optionally, adding an adjudication window buffer to the latest of the next adjudication dates. The system determines the final alignment date, optionally adding additional time for processing of the aligned prescriptions. The system also calculates short-fill parameters for any prescriptions for which the customer would exhaust the amount of medication remaining prior to the calculated alignment date. The aligned prescriptions and, where necessary, short fills, are delivered to the customer prior to the alignment date.

In some embodiments, the method may include marking a prescription where the delivery of a required short fill for a medication cannot occur before the customer runs out of the medication and/or when the pharmacy cannot short fill a prescription. If a short fill is not possible the system acting in accordance with the method fills the prescription with a full fill and the method updates the alignment parameters accordingly.

In other embodiments, the method may include recalculating the amount of medication supplied to the customer in a short fill if the customer declines an alternate delivery method in an instance where the delivery of the short fill for a medication cannot occur before the customer runs out of medication using the customer's preferred delivery method.

In one embodiment, a method facilitates alignment of refill dates associated with a plurality of prescriptions for a customer to a single alignment date. The method includes receiving a selection of a plurality of prescriptions to align and determining, for each of the plurality of selected prescriptions, a remaining day supply indicative of a number of days of medication the customer has remaining. A next adjudication date is calculated for each of the plurality of selected prescriptions, and the latest of the calculated next adjudication dates is selected as a latest adjudication date. The method also includes calculating an alignment adjudication date and a final alignment date. For each of the plurality of selected prescriptions, the method includes determining whether a short fill is required so that the customer does not exhaust the remaining day supply of the prescribed medication before the final alignment date. For each prescription requiring a short fill, the method includes calculating a short-fill day supply, determining a date by which the customer will receive the short fill, and determining whether the customer will exhaust the remaining day supply of the prescribed medication before the date by which the customer will receive the short fill for the prescription. If the customer will receive the required short fill for the prescription before exhausting the remaining day supply of the prescribed medication, the method includes calculating a short-fill quantity for the prescription. Additionally, the method includes marking any prescription for which a short fill is required, but for which the short fill is not possible. If none of the prescriptions are marked, the method includes filling and providing to the customer the short-fill quantity for any prescription requiring a short fill, adjudicating each of the selected prescriptions on or after the alignment adjudication date, filling each of the selected prescriptions, and providing each of the medications corresponding to the selected prescriptions to the customer by the final alignment date. If one or more of the prescriptions are marked, the method includes recalculating the next adjudication date for each of the selected prescriptions, selecting the recalculated next adjudication date that occurs on the latest date as the latest adjudication date, recalculating the alignment adjudication date, and recalculating the final alignment date. Also, if one or more prescriptions are marked the method further includes determining, with the recalculated adjudication dates, whether a short fill is required so that the customer does not exhaust the remaining day supply of the medication before the recalculated final alignment date, recalculating the short-fill day supply for any prescription requiring a short fill, adjudicating each of the selected prescriptions on or after the recalculated alignment adjudication date, filling each of the prescriptions, and providing each of the medications corresponding to the selected prescriptions to the customer by the recalculated final alignment date. Calculating the final alignment date may include adding one or more days to the alignment adjudication date for processing the prescriptions and providing the medications to the customer. Calculating a next adjudication date may include determining a number of days corresponding to a percentage of a prescribed day supply for the medication. Determining a date by which the customer will receive the short fill for a prescription requiring a short fill may include adding one or more days to the next adjudication date for the prescription for processing the prescription and providing the medication to the customer. Providing each of the medications to the customer may include providing the medications to the customer by a shipping service or a postal service. In some embodiments, short fills are not adjudicated. In some embodiments, the customer comprises two or more people, and where the customer comprises two or more people, the two or more people may be members of the same family or may be members of the same household. Where the prescription is provided to the customer by a shipping service or a postal service, the method may include determining whether the customer will receive a required short fill for the prescription prior to exhausting the remaining day supply of the medication and, if not, requesting the customer to pick up the short fill of the prescription from a retail location, indicating the retail pickup of the short fill of the prescription if the customer agrees to retail pickup, and recalculating the short-fill day supply if the customer does not agree to retail pickup. Providing to the customer the short fill quantity for any prescription requiring a short fill may include providing the short fill to the customer by a preferred delivery method when, using the preferred delivery method, the customer will receive the short fill before exhausting the remaining day supply of the medication, and evaluating an alternate delivery method where using the preferred delivery method would result in the customer exhausting the remaining day supply of the medication before receiving the short fill.

In one embodiment, a method facilitates alignment of refill dates associated with a plurality of prescriptions for a customer to a single alignment date. The method includes receiving a selection of a plurality of prescriptions to align and determining, for each of the plurality of selected prescriptions, a remaining day supply indicative of a number of days of medication the customer has remaining. The method also includes calculating a final alignment date. For each of the plurality of selected prescriptions, the method includes determining whether a short fill is required so that the customer does not exhaust the remaining day supply of the medication before the final alignment date. For each prescription that requires a short fill, the method includes calculating one or both of a short-fill day supply and a short-fill quantity, filling the short fill based on the short-fill day supply or the short-fill quantity, and providing to the customer any required short fill, based on the short-fill day supply or the short-fill quantity for the medication. The method also includes filling each of the selected prescriptions. The method may also include providing to the customer by the final alignment date each of the medications corresponding to the selected prescriptions. Calculating the final alignment date may include complying with at least one adjudication rule set by a third-party payor, which may include calculating a next adjudication date for each of the selected prescriptions, selecting the next adjudication date occurring on the latest date as a latest adjudication date, calculating an alignment adjudication date, and selecting the final alignment date using the alignment adjudication date. Selecting the final alignment date using the alignment adjudication date may include adding one or more days to the alignment adjudication date for processing the prescriptions and providing the medications to the customer. Calculating a next adjudication date may include determining a number of days corresponding to a percentage of a prescribed day supply for the medication. In some embodiments, filling and providing to the customer any required short fill comprises selecting one or more of the required short fills and providing the selected one or more short fills to the customer without adjudicating the one or more short fills. The one or more selected short fills may be selected because adjudicating the one or more selected short fills would delay the final alignment date. In some embodiments, short fills are not adjudicated. In some embodiments, the customer is two or more people, and in embodiments where the customer is two or more people, the two or more people are members of the same family or are members of the same household.

In one embodiment, a method facilitates alignment of refill dates associated with a plurality of prescriptions for a customer to a single alignment date. The method includes receiving a selection of a plurality of prescriptions to align and determining, for each of the plurality of selected prescriptions, a remaining day supply indicative of a number of days of medication the customer has remaining. The method also includes calculating a final alignment date. For each of the plurality of selected prescriptions, the method includes determining whether a short fill is required so that the customer does not exhaust the remaining day supply of the medication before the final alignment date. For each prescription that requires a short fill, the method includes calculating one or both of a short-fill day supply and a short-fill quantity, filling the short fill based on either the short-fill day supply or the short-fill quantity, and providing to the customer any required short fill, based on the short-fill day supply or the short-fill quantity for the medication. The method also includes filling each of the selected prescriptions. The method also includes determining a date by which the customer will receive each required short fill, and using the date by which the customer will receive the required short fill to calculate one or both of the short-fill day supply and the short-fill quantity of the medication corresponding to the prescription if the customer will receive the short fill for the prescription before exhausting the remaining day supply of the medication. Determining a date by which the customer will receive the short fill may include adding one or more days to the next adjudication date for the prescription for processing the prescription and providing the medication to the customer. Where providing prescriptions to the customer includes a method involving lead time, filling and providing to the customer any required short fill, based on either the short-fill quantity or the short-fill day supply, may include determining, for any prescription that requires a short fill, whether the customer will receive the short fill for the prescription before the customer exhausts the remaining day supply of the medication corresponding to the prescription. For any prescription for which the customer will not receive the short fill before exhausting the remaining day supply of the medication corresponding to the prescription, the method may include requesting the customer to pick up the short fill of the prescription from a retail location, marking the short fill of the prescription for retail pickup if the customer agrees to retail pickup, recalculating one or both of the short-fill day supply and the short-fill quantity if the customer does not agree to retail pickup, and determining whether any prescriptions are marked. Filling and providing to the customer any required short fill, based on either the short-fill quantity or the short-fill day supply for the prescription, may include delivering to the customer at a retail location any prescriptions marked for retail pickup.

In one embodiment, a method facilitates alignment of refill dates associated with a plurality of prescriptions for a customer to a single alignment date. The method includes receiving a selection of a plurality of prescriptions to align and determining, for each of the plurality of selected prescriptions, a remaining day supply indicative of a number of days of medication the customer has remaining. The method also includes calculating a final alignment date. For each of the plurality of selected prescriptions, the method includes determining whether a short fill is required so that the customer does not exhaust the remaining day supply of the medication before the final alignment date. For each prescription that requires a short fill, the method includes calculating one or both of a short-fill day supply and a short-fill quantity, filling the short fill based on either the short-fill day supply or the short-fill quantity, and providing to the customer any required short fill, based on either the short-fill day supply or the short-fill quantity of the medication. The method also includes filling each of the selected prescriptions. The method further includes determining a date by which the customer will receive each required short fill, and using the date by which the customer will receive the required short fill to calculate one or both of the short-fill quantity and the short-fill day supply of the medication corresponding to the prescription if the customer will receive the short fill for the prescription before exhausting the remaining day supply of the medication. Additionally, the method includes marking any prescription for which a short fill is required, but for which the customer cannot receive required short fill before exhausting the remaining day supply of the medication. If one or more prescriptions are marked the method includes updating the next adjudication date for each of the selected prescriptions, recalculating the final alignment date, determining, with the recalculated adjudication dates, whether a short fill is required so that the customer does not exhaust the remaining day supply of the medication before the recalculated final alignment date, and recalculating one or both of the short-fill day supply and the short-fill quantity for any prescription requiring a short fill.

In one embodiment, a method facilitates alignment of refill dates associated with a plurality of prescriptions for a customer to a single alignment date. The method includes receiving a selection of a plurality of prescriptions to align and determining, for each of the plurality of selected prescriptions, a remaining day supply indicative of a number of days of medication the customer has remaining. The method also includes calculating a final alignment date. For each of the plurality of selected prescriptions, the method includes determining whether a short fill is required so that the customer does not exhaust the remaining day supply of the medication before the final alignment date. For each prescription that requires a short fill, the method includes calculating one or both of a short-fill day supply and a short-fill quantity, filling the short fill based on either the short-fill day supply or the short-fill quantity, and providing to the customer any required short fill, based on either the short-fill day supply or the short-fill quantity of the medication. The method also includes filling each of the selected prescriptions. The method further includes determining a date by which the customer will receive each required short fill, and using the date by which the customer will receive the required short fill to calculate one or both of the short-fill quantity and the short-fill day supply of the medication corresponding to the prescription if the customer will receive the short fill for the prescription before exhausting the remaining day supply of the medication. Where providing prescriptions to the customer includes a method involving lead time, filling and providing to the customer any required short fill, based on either the short-fill quantity or the short-fill day supply, may include determining, for any prescription that requires a short fill, whether the customer will receive the short fill for the prescription before the customer exhausts the remaining day supply of the medication. For any prescription for which the customer will not receive the short fill for the prescription before exhausting the remaining day supply of the medication, the method may include requesting the customer to pick up the short fill of the prescription from a retail location, marking the short fill of the prescription for retail pickup if the customer agrees to retail pickup, recalculating the short-fill day supply or the short-fill quantity if the customer does not agree to retail pickup, and determining whether any prescriptions are marked. The method also includes, for prescriptions marked for retail pickup, delivering the corresponding short fill to the customer at a retail location.

In one embodiment, a method facilitates alignment of refill dates associated with a plurality of prescriptions for a customer to a single alignment date. The method includes receiving a selection of a plurality of prescriptions to align and determining, for each of the plurality of selected prescriptions, a remaining day supply indicative of a number of days of medication the customer has remaining. The method also includes calculating a final alignment date. For each of the plurality of selected prescriptions, the method includes determining whether a short fill is required so that the customer does not exhaust the remaining day supply of the medication before the final alignment date. For each prescription that requires a short fill, the method includes calculating one or both of a short-fill day supply and a short-fill quantity, filling the short fill based on either the short-fill day supply or the short-fill quantity, and providing to the customer any required short fill, based on the short-fill day supply or the short-fill quantity for the medication. The method also includes filling each of the selected prescriptions. The method further includes determining a date by which the customer will receive each required short fill, and using the date by which the customer will receive the required short fill to calculate one or both of the short-fill day supply and the short-fill quantity of the medication corresponding to the prescription if the customer will receive the short fill for the prescription before exhausting the remaining day supply of the medication. The method also includes determining whether each short fill is possible using a preferred delivery method, and determining for each short fill that is possible with the preferred delivery method, whether the customer will receive the short fill before exhausting the remaining day supply of the medication. For each required short fill that is not possible using the preferred delivery method, and for each required short fill that is possible using the preferred delivery method but for which the customer will not receive the short fill before exhausting the remaining day supply of the medication, the method includes determining whether the short fill is possible using an alternate delivery method. For any short fill that is not possible using the alternate delivery method, and for any short fill that the customer does not want to use the alternate delivery method, the method includes marking the short fill as not possible. For each required short fill that is possible by the alternate delivery method and for which the customer wants to use the alternate delivery method, the method includes determining whether the customer will receive the short fill before exhausting the remaining day supply of the medication.

In one embodiment, a method facilitates alignment of refill dates associated with a plurality of prescriptions for a customer to a single alignment date. The method includes receiving a selection of a plurality of prescriptions to align and determining, for each of the plurality of selected prescriptions, a remaining day supply indicative of a number of days of medication the customer has remaining. The method also includes calculating a final alignment date. For each of the plurality of selected prescriptions, the method includes determining whether a short fill is required so that the customer does not exhaust the remaining day supply of the medication before the final alignment date. For each prescription that requires a short fill, the method includes calculating one or both of a short-fill day supply and a short-fill quantity, filling the short fill based on either the short-fill day supply or the short-fill quantity, and providing to the customer any required short fill, based on either the short-fill day supply or the short-fill quantity of the medication. The method also includes filling each of the selected prescriptions. The method further includes determining a date by which the customer will receive each required short fill, and using the date by which the customer will receive the required short fill to calculate one or both of the short-fill quantity and the short-fill day supply of the medication corresponding to the prescription if the customer will receive the short fill for the prescription before exhausting the remaining day supply of the medication. Where providing prescriptions to the customer includes a first method involving lead time, filling and providing to the customer any required short fill, based on either the short-fill quantity or the short-fill day supply, may include determining, for any prescription that requires a short fill, whether the customer will receive the short fill for the prescription before the customer exhausts the remaining day supply of the medication corresponding to the prescription. The method may also include evaluating an alternate method for providing the medications to the customer if using the first method involving lead time will result in the customer exhausting the remaining day supply of the medication corresponding to the prescription before receiving the short fill for the prescription.

In one embodiment, a system facilitates alignment of refill dates associated with a plurality of prescriptions for a customer to a single alignment date. The system includes a network, a computer coupled to the network, and a database coupled to the computer. The system also includes an alignment engine for determining parameters associated with the alignment of the plurality of prescriptions. The alignment engine is configured to receive a selection of a plurality of prescriptions to align. The alignment engine is further operative to calculate a final alignment date and a short-fill parameter. The alignment engine may be configured to determine a latest adjudication date from a plurality of calculated next adjudication dates, in compliance with a rule determined by a third-party payor or a regulatory agency. Additionally, the alignment engine may be configured to retrieve information from the database and calculate a parameter required to determine compliance with the rule determined by the third-party payor or the regulatory agency. The rule may be an adjudication rule, and calculating a parameter required to determine compliance with the rule may include calculating a percent-consumption period. Additionally, calculating a short-fill parameter may include calculating a short-fill day supply, calculating a short-fill quantity, or calculating a short-fill delivery date.

In one embodiment, a method facilitates alignment of refill dates associated with a plurality of prescriptions for a customer to a single alignment date. The method includes receiving a selection of a plurality of prescriptions to align and determining, for each of the plurality of selected prescriptions, a remaining day supply indicative of a number of days of medication the customer has remaining. The method also includes calculating a final alignment date. The method also includes determining, for each of the plurality of selected prescriptions, whether the customer will exhaust the remaining day supply of the medication before the final alignment date, and filling and providing one intermediate fill of the medication for each of the selected prescriptions for which the customer will exhaust the remaining day supply of the medication before the alignment date. The method further includes filling each of the selected prescriptions. For each of the medications for which the one intermediate fill is provided, the one intermediate fill may be a short fill, a full fill, or an overfill.

DETAILED DESCRIPTION

Figure 1A:
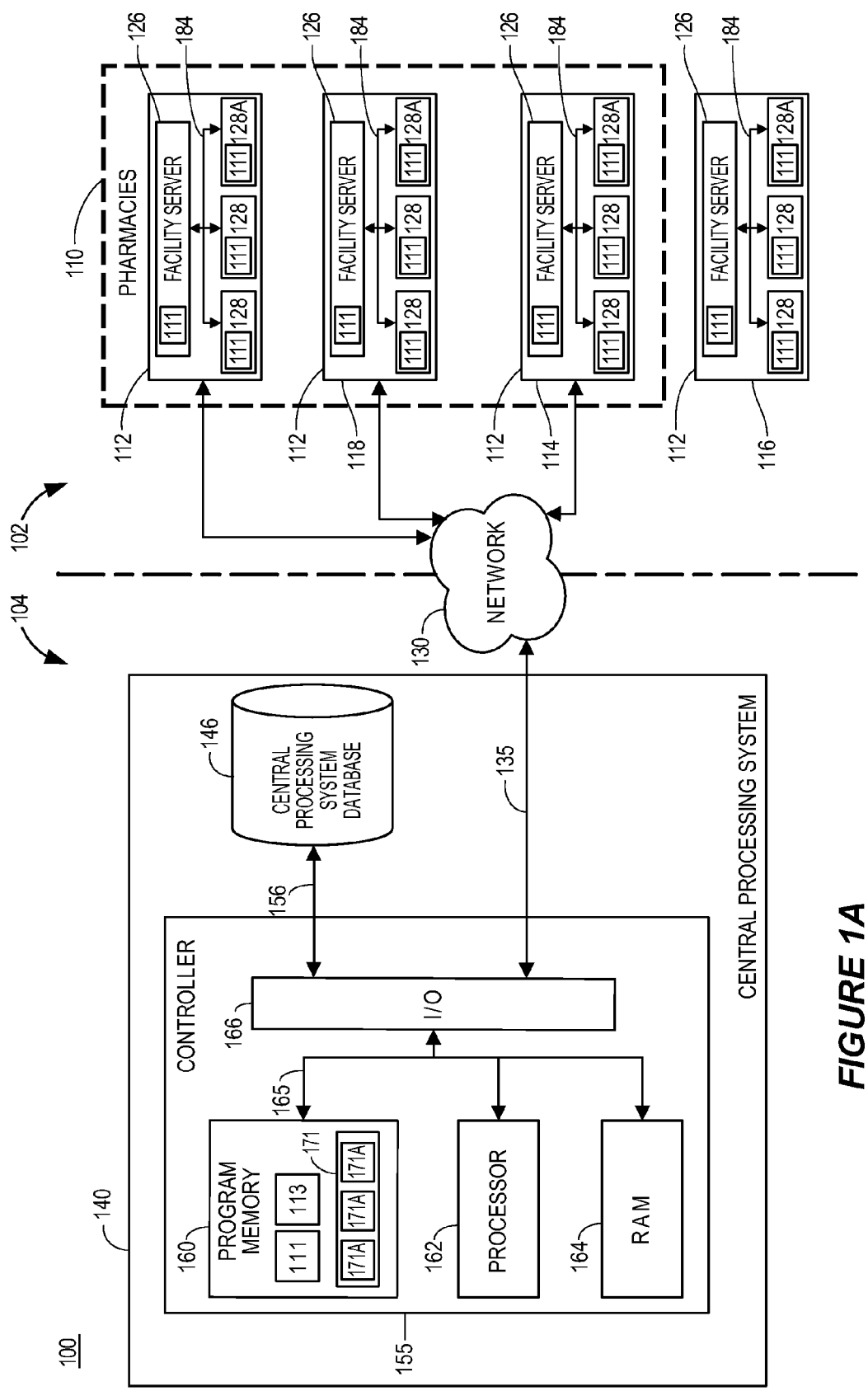
FIG. 1A illustrates a block diagram of a computer network and system on which an exemplary prescription alignment system may operate in accordance with the described embodiments.
Figure 1B:
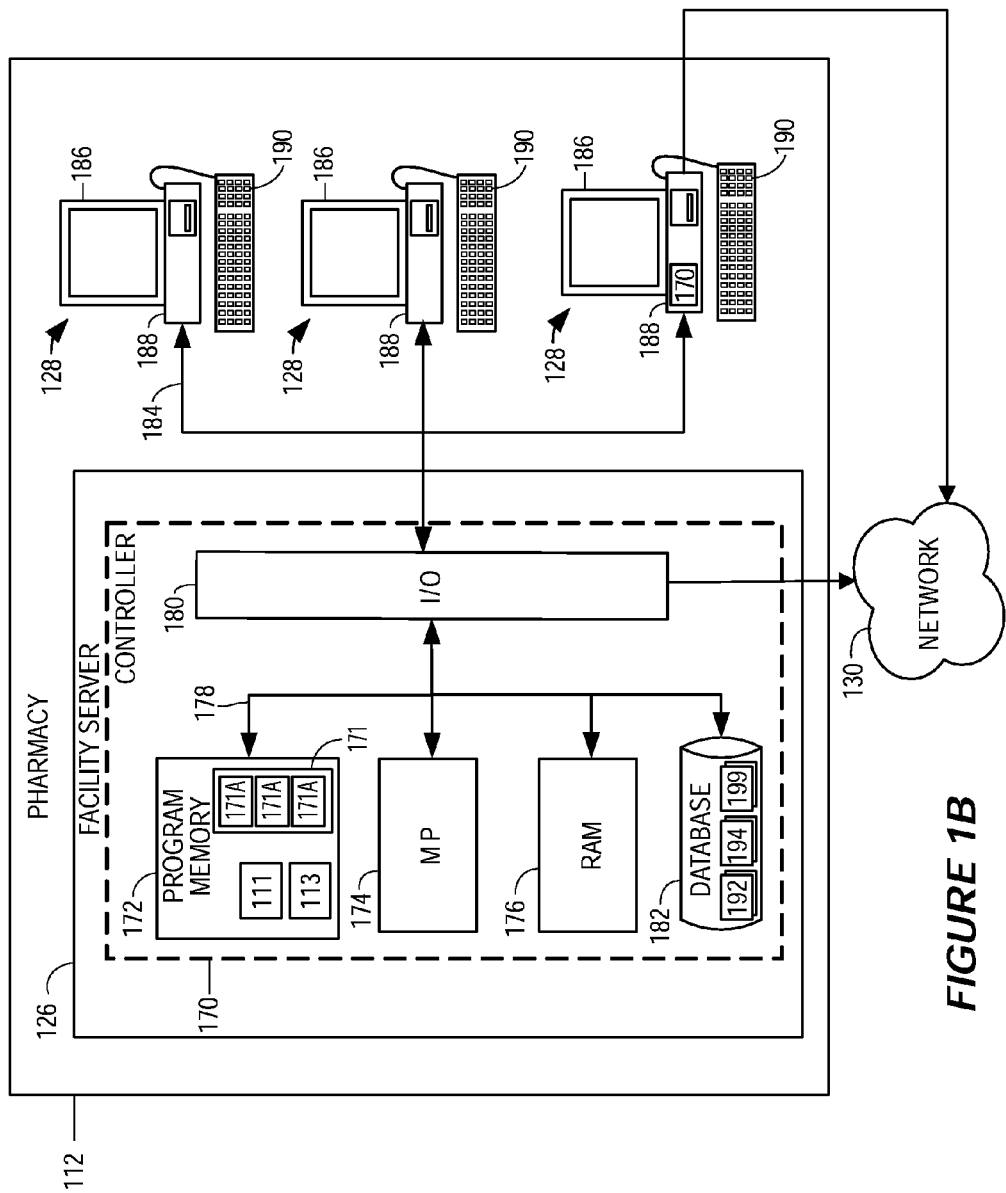
FIG. 1B illustrates a block diagram of a computer server and computer terminals on which an exemplary prescription alignment system may operate in accordance with the described embodiments.
Figure 1C:
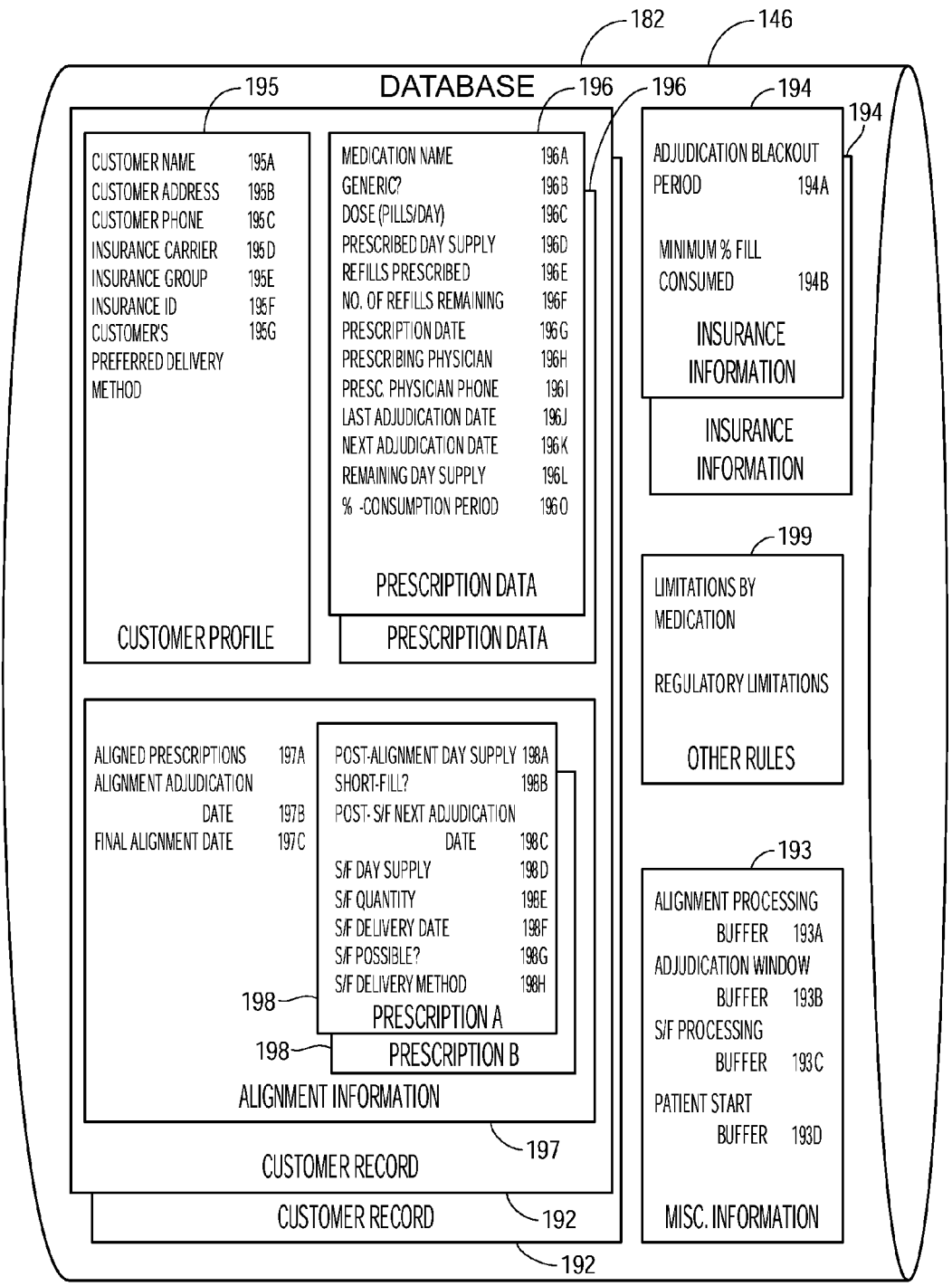
FIG. 1C depicts exemplary data in a database depicted in either of FIG. 1A or FIG. 1B, in accordance with the described embodiments.

FIGS. 1A, 1B, and 1C illustrate various aspects of an exemplary architecture implementing a prescription alignment system 100. In particular, FIG. 1A illustrates a block diagram of the exemplary prescription alignment system 100. The high-level architecture includes both hardware and software applications, as well as various data communications channels for communicating data between the various hardware and software components. The prescription alignment system 100 may be roughly divided into front-end components 102 and back-end components 104. The front-end components 102 are primarily disposed within a retail network 110 including one or more pharmacies 112. The pharmacies 112 may be located, by way of example rather than limitation, in separate geographic locations from each other, including different areas of the same city, different cities, or even different states. The front-end components 102 comprise a number of pharmacy workstations 128. The pharmacy workstations 128 are local computers located in the various pharmacies 112 throughout the retail network 110 and executing various pharmacy management-related applications. Pharmacists and other pharmacy personnel, referred to collectively herein simply as "pharmacists" (not shown), use the pharmacy workstations 128 to access customer information, enter new prescriptions, access insurance and payment information and so forth. Each of the pharmacies 112 may be, for example, an in-store retail pharmacy, an on-line pharmacy, a mail-order pharmacy, a long-term care pharmacy, a workplace/on-site pharmacy, or a specialty pharmacy. Retail network 110 may also include one or more warehouses or central-filling facilities 118. The warehouses or central-filling facilities 118 may distribute medications to the various retail pharmacies 112 in the retail network 110, or may distribute medications directly to customers. Of course, the pharmacy 112 may also be a stand-alone pharmacy 116 (i.e., not part of any retail network or chain).

As used herein, the term medication may be read to mean any substance that may be distributed by a pharmacy or by a pharmacist, including those substances that may be obtained without a prescription (i.e., "over the counter" substances such as vitamins). Thus, while the embodiments described herein contemplate the alignment of refills related to prescription medications, other substances (e.g., nutritional supplements, over-the-counter medications, etc.) may also be dispensed with one or more prescription medications. The refill of these other substances may likewise be aligned with one or more prescription medications. Of course, the methods described herein may also be used to align refills of two or more non-prescription substances with each other, even if none of the two or more non-prescription substances is aligned with a prescription medication.

Returning now to FIG. 1A, those of ordinary skill in the art will recognize that the front-end components 102 could also comprise a plurality of facility servers 126 and client device terminals 128A disposed at the plurality of pharmacies 112, instead of, or in addition to, a plurality of pharmacy workstations 128. Each of the pharmacies 112 may include one or more facility servers 126 that may facilitate communications between the client device terminals 128A and the back-end components 104 via a digital network 130, described below, and may store information for a plurality of customers/employees/accounts/etc. associated with each facility. Of course, a local digital network 184 may also operatively connect each of the workstations 128 to the facility server 126. Unless otherwise indicated, any discussion of the workstations 128 also refers to the facility servers 126 and the client device terminals 128A, and vice versa. Moreover, environments other than the pharmacies 112, such as the kiosks, call centers, and Internet interface terminals contemplated in U.S. patent application Ser. No. 11/781,926, entitled "System and Method of Prescription Alignment," filed Jul. 23, 2007, may employ the workstations 128, the client device terminals 128A, and the servers 126. As used herein, the term "pharmacy" refers to any of these points of contact (e.g., call centers, kiosks, Internet interface terminals, etc.) in addition to the retail pharmacies 112, warehouses 116, etc. described above.

The front-end components 102 communicate with the back-end components 104 via the digital network 130. The digital network 130 may be a proprietary network, a secure public Internet, a virtual private network or some other type of network, such as dedicated access lines, plain ordinary telephone lines, satellite links, combinations of these, etc. Where the digital network 130 comprises the Internet, data communication may take place over the digital network 130 via an Internet communication protocol. The back-end components 104 include a prescription alignment central processing system 140. The prescription alignment central processing system 140 may include one or more computer processors 162 adapted and configured to execute various software applications and components of the prescription alignment system 100, in addition to other software applications, such as a medication management system. The central processing system 140 further includes a database 146. The database 146 is adapted to store data related to the operation of the pharmacies 112 and the prescription alignment system 100. The central processing system 140 may access data stored in the database 146 when executing various functions and tasks associated with the operation of the prescription alignment system 100.

Although the prescription alignment system 100 is shown to include one prescription alignment central processing system 140 and four pharmacies 112, it should be understood that different numbers of computers and pharmacies may be utilized. For example, the digital network 130 may interconnect the system 100 to a plurality of included central processing systems 140 and hundreds of included pharmacies 112 within the retail network 110. According to the disclosed example, this configuration may provide several advantages, such as, for example, enabling near real-time uploads and downloads of information as well as periodic uploads and downloads of information. This provides for a primary backup of all the information generated in the process of updating and accumulating pharmacy data. Alternatively, some of the pharmacies 112, such as the pharmacy 116, may be separate from the digital network 130, storing the necessary data locally on the facility server 126 and/or the workstations 128.

FIG. 1A also depicts one possible embodiment of the central processing system 140. The central processing system 140 may have a controller 155 operatively connected to the database 146 via a link 156 connected to an input/output (I/O) circuit 166. It should be noted that, while not shown, additional databases may be linked to the controller 155 in a known manner.

The controller 155 includes a program memory 160, the processor 162 (may be called a microcontroller or a microprocessor), a random-access memory (RAM) 164, and the input/output (I/O) circuit 166, all of which are interconnected via an address/data bus 165. It should be appreciated that although only one microprocessor 162 is shown, the controller 155 may include multiple microprocessors 162. Similarly, the memory of the controller 155 may include multiple RAMs 164 and multiple program memories 160. Although the I/O circuit 166 is shown as a single block, it should be appreciated that the I/O circuit 166 may include a number of different types of I/O circuits. The RAM(s) 164 and the program memories 160 may be implemented as semiconductor memories, magnetically readable memories, and/or optically readable memories, for example. A link 135 may operatively connect the controller 155 to the digital network 130 through the I/O circuit 166.

FIG. 1B depicts one possible embodiment of the front-end components 102 located in one or more of the pharmacies 112 from FIG. 1A. Although the following description addresses the design of the pharmacies 112, it should be understood that the design of one or more of the pharmacies 112 may be different than the design of others of the pharmacies 112. Also, each of the pharmacies 112 may have various different structures and methods of operation. It should also be understood that while the embodiment shown in FIG. 1B illustrates some of the components and data connections that may be present in a pharmacy 112, it does not illustrate all of the data connections that may be present in a pharmacy 112. For exemplary purposes, one design of a pharmacy is described below, but it should be understood that numerous other designs may be utilized.

Each of the pharmacies 112 has one or more pharmacy workstations 128 and/or a facility server 126. The digital network 184 operatively connects the facility server 126 to the plurality of workstations 128 and/or to the client device terminals 128A. The digital network 184 may be a wide area network (WAN), a local area network (LAN), or any other type of digital network readily known to those persons skilled in the art. The digital network 130 may operatively connect the facility server 126, the workstations 128, and/or the client device terminals 128A to the central processing system 140.

Each workstation 128, client device terminal 128A, or facility server 126 includes a controller 170. Similar to the controller 155 from FIG. 1A, the controller 170 includes a program memory 172, a microcontroller or a microprocessor (MP) 174, a random-access memory (RAM) 176, and an input/output (I/O) circuit 180, all of which are interconnected via an address/data bus 178. In some embodiments, the controller 170 may also include, or otherwise be communicatively connected to, a database 182. The database 182 (and/or the database 146 of FIG. 1A) includes data such as customer records 192, insurer information records 194, and other rules 199 and miscellaneous information 193 (as depicted in FIG. 1C). As discussed with reference to the controller 155, it should be appreciated that although FIG. 1B depicts only one microprocessor 174, the controller 170 may include multiple microprocessors 174. Similarly, the memory of the controller 170 may include multiple RAMs 176 and multiple program memories 172. Although the figure depicts the I/O circuit 180 as a single block, the I/O circuit 180 may include a number of different types of I/O circuits. The controller 170 may implement the RAM(s) 176 and the program memories 172 as semiconductor memories, magnetically readable memories, and/or optically readable memories, for example.

Either or both of the program memories 160 and 172 may also contain an alignment engine 171, for execution within the processors 162 and 174, respectively. The alignment engine 171 may perform the various tasks associated with the alignment method, and may be a single module 171A or a plurality of modules 171A. By way of example and not limitation, the alignment engine 171 or the modules 171A within the alignment engine 171 may: receive a selection of a plurality of prescriptions to align; determine a latest adjudication date from a plurality of calculated adjudication dates; calculate parameters associated with a short-fill of a prescription, such as a short-fill day supply, a short-fill quantity, or a short-fill delivery date; calculate a final alignment date for a plurality of prescriptions; retrieve information from the database 182 (or the database 146); calculate a parameter, such as a percent-consumption period, required to determine compliance with a rule determined by a third-party payor or a regulatory agency; calculate adjudication dates associated with one or more prescriptions; adjudicate one or more prescriptions; fill prescriptions; cause prescriptions to be shipped to the customer or to a retail location; etc. Each of the modules 171A may execute one or more of the various parts of the alignment method described below with reference to FIGS. 2A and 2B.

In addition to the controller 170, the workstations 128 and the client device terminals 128A may further include a display 186 and a keyboard 190 as well as a variety of other input/output devices (not shown) such as a scanner, printer, mouse, touch screen, track pad, track ball, isopoint, voice recognition system, digital camera, etc. A pharmacy employee may sign on and occupy each workstation 128 or client device terminal 128A to assist the pharmacy employee in performing his or her duties. Pharmacy employees may sign onto the workstation 128 or the client device terminal 128A using any available technique, such as entering a user name and password. If a pharmacy employee signs on to the system using a client device terminal 128A, the network 184 communicates this information to the facility server 126, so that the controller 170 may identify which pharmacy employees are signed onto the system 100 and which workstation 128 or client device terminal 128A the employee is signed onto. This may be useful for record keeping and/or monitoring the pharmacy employees' productivity as well as in record-keeping.

Various software applications resident in the front-end components 102 and the back-end components 104 implement the prescription alignment methods, and provide various user interface means to allow users (i.e., pharmacists and/or customers) to access the system 100. One or more of the front-end components 102 and/or the back-end components 104 may include a user-interface application 111 for allowing a user, such as the pharmacist or customer service representative, to input and view data associated with the system 100. In one embodiment, the user-interface application 111 is a web browser client, and the facility server 126 or the central-processing system 140 implements a server application 113 for providing data to the user-interface application 111. However, the user-interface application 111 may be any type of interface, including a proprietary interface, and may communicate with the facility server 126 or the central processing system 140 using any type of protocol including, but not limited to, file transfer protocol (FTP), telnet, hypertext-transfer protocol (HTTP), etc. Moreover, the user interface application 111 may be running on one of the workstations 128 in a pharmacy 112 (as when the pharmacist is accessing the system) or may be running on an Internet interface terminal (not shown) (as when a customer is requesting and configuring alignment of the customer's prescriptions). The information sent to the workstations 128 and to the client device terminals 128A from the facility server 126 and/or the central processing system 140 includes data retrieved from the database 146 and/or the database 182. The central processing system 140 and/or the facility server 126 may implement any known protocol compatible with the user-interface application 111 running on the workstations 128 and the client device terminals 128A and adapted to the purpose of receiving and providing the necessary customer information via the digital network 130 and/or the digital network 184.

For purposes of implementing the prescription alignment system 100, the primary point of contact with the customer is through the pharmacy 112. As used herein, the term "customer" may be, by way of example, a patient (i.e., the person named on the prescription), a guardian (e.g., the parent of a child named on the prescription), a care-giver (i.e., anyone who takes care of a patient or picks up the medication on the patient's behalf), etc. Moreover, the term "customer" is not limited to a single person, but may instead be any person or persons having a reason to align a group of prescriptions. For example, a customer could be a care-giver responsible for various patients, for which caregiver it would be convenient to align prescriptions for the various patients so as to avoid having to order and/or retrieve prescription refills on an overwhelming number of dates. Or, for example, a customer could be a family wherein multiple family members have prescriptions which, if aligned, would reduce the burden of ordering and/or retrieving the various medications prescribed to the family members. In any event, while the term "customer" is used interchangeably with the term "patient," in this specification the term "customer" is used primarily so as to avoid confusion. Thus, a customer may be a patient (as where a person picks up his/her own prescriptions), but a customer may also be, by way of example, a parent picking up a prescription for a child (i.e., a guardian), a husband picking up a prescription for his wife, a home-care nurse picking up a prescription for one or more patients, a care facility director (or other personnel) picking up prescriptions for one or more patients, etc. Also, as mentioned above, the pharmacy 112 may be any of the channels through which the entity implementing the prescription alignment system 100 serves its pharmacy customers. Thus, the pharmacy 112 may be a retail pharmacy 112 in the customer's neighborhood (or any other drug store in a drug store chain), an on-line pharmacy or an on-line interface to a pharmacy 112 or to a retail network 110 (where the customer uses a web-browser to communicate with the server application 113), a phone/touchtone interface to a pharmacy 112 or to a retail network 110 (where the customer uses a phone service to communicate with the server application 113), a mail-order pharmacy, a central-filling facility, a specialty pharmacy, or any other type of pharmacy affiliated with the entity implementing the prescription alignment system 100. In one embodiment, a pharmacist, other pharmacy staff, or a customer service representative (all referred to herein simply as "the pharmacist") invokes the prescription alignment system 100 while interacting with a customer at a pharmacy 112 or over the telephone (e.g., from a retail pharmacy 112, or a call center). The pharmacist will have access to one of the pharmacy workstations 128 or to one of the client device terminals 128A and may invoke the prescription alignment system 100 when he or she fills the customer's prescription. In another embodiment, the customer invokes the prescription alignment system 100 (e.g., at a kiosk, via an Internet interface terminal, on a mail-in form, etc.). Alternatively, the prescription alignment system 100 may be invoked automatically for each new prescription entered (e.g., by reminding the pharmacist to ask whether the customer would like to align his or her prescriptions) or by a broader system, such as a medication management system.

As described above, one or both of the databases 146 and 182, illustrated in FIGS. 1A and 1B, respectively, include various information about the pharmacy's customers and the prescriptions filled by the pharmacy, as well as various business information including, but not limited to, information associated with third-party payors (e.g., insurance companies), employee information, and the like. FIG. C depicts some of the exemplary data that the system 100 may store on the databases 146 and 182. The databases 146 and/or 182 contain a customer record 192 for every customer who purchases his/her medication at one of the pharmacies 112 (or via a call center, website, etc.). The customer record 192 contains important information about the customer and the various pharmacy services that have been invoked by, or on behalf of, the customer in a customer profile 195. The customer profile 195 includes basic biographical information about the customer, such as a customer name 195A, a customer address 195B, a customer phone number 195C, an insurance carrier 195D associated with the customer, an insurance group number 195E for the customer, an insurance ID number 195F for the customer, a preferred delivery method 195G, etc. Additionally, the customer profile 195 may include other information such as credit card information or other payment information, one or more customer e-mail addresses, user name and/or password information, online security question/answer information, etc. Of course, the customer record 192 may also include other or less information than that described.

The customer record 192 also includes prescription data 196 for each prescription filled by the pharmacy for the customer. The prescription data 196 generally include, but are not limited to: a name 196A of the medication; an indication 196B whether a generic may be substituted; a dose (i.e., pills per day) 196C of the medication; a number of days of medication to be dispensed (also referred to herein as a "day supply" or a "prescribed day supply") 196D; a number of refills prescribed 196E; a number of refills remaining 196F; a prescription date 196G; a prescribing physician 196H; a phone number 196I for the prescribing physician; a date on which the prescription was most recently adjudicated (also referred to herein as a "last adjudication date") 196J; a calculated date on which the prescription may next be adjudicated (also referred to herein as a "next adjudication date") 196K for the prescription; a remaining day supply 196L for the prescription; and a percent-consumption period 196O indicating the number of days it would take to consume the required minimum percent-fill consumed 194B of the fill for the prescription). Of course, the prescription data 196 need not include all of the information above, such as when the system 100 determines some information (e.g., the next adjudication date 196K) but does not store it, or stores it some place other than with the prescription data 196 in the database 146 or the database 182. Moreover, the prescription data 196 may include additional information not mentioned above.

Additionally, the customer record 192 includes alignment information 197. The alignment information 197 generally includes information related to the final alignment of the prescriptions, including, in part, a list of prescriptions selected for alignment 197A, an alignment adjudication date 197B, and a final alignment date 197C. Additionally, the alignment information 197 includes, for each of the prescriptions selected for alignment, information 198 specific to the alignment of the prescription. For example, aligning the plurality of selected prescriptions may require adjusting the day supply for one fill for each of one or more of the selected prescriptions by, for example, dispensing more of the medication ("overfilling") or less of the medication ("underfilling" or "short-filling") such that the customer exhausts the supply of a first medication at the same time as the supply of a second medication. An underfilled prescription is referred to herein as a "short fill." Each short fill may have an associated post short-fill next adjudication date 198C, an associated short-fill day supply 198D, indicating the number of days of medication dispensed, etc. The information 198 includes, for each prescription, a post-alignment day supply 198A (indicating for the medication the day supply to be dispensed on or around the alignment adjudication date and, presumably, for each refill thereafter), an indication 198B of whether the prescription requires a short-fill, the post short-fill next adjudication date 198C, the short-fill day-supply 198D, a short-fill quantity 198E, a short-fill delivery date 198F, and an indication 198G of whether a short fill is possible. Of course, the alignment information 197, including the information 198, may, in some embodiments, include more or less information than described above. Additionally, the alignment information 197 may vary over time. For example, when a customer adds a new medication, the alignment information 197, including the final alignment date 197C, may change to accommodate the newly prescribed medication. Moreover, in some circumstances (e.g., where there are no applicable adjudication rules), it may be possible to deliver all of any required short-fills on the same date and, therefore, the short-fill delivery date 198F for each required short fill could be the same.

The database 182 and/or the database 146 may also include rules related to the filling and/or re-filling of prescriptions. In particular, records 193 include generically applicable information related to the alignment process, described with reference to FIGS. 2A and 2B, records 194 include rules promulgated by third-party payors (i.e., insurance companies), and records 199 include prescription limitations (i.e., limitations placed on a prescription by a physician or a drug manufacturer), and other rules (e.g., regulations related to specific drugs) that may place limitations on the when, and how often, a customer refills a prescription, or how much of the prescribed medication the customer receives. These limitations complicate the alignment process by constraining various aspects of the refill process and, in many instances, delay the final alignment date 197C of prescription refills.

Third parties promulgate the majority of the rules discussed above, which rules relate specifically to the adjudication of the prescription (i.e., making a claim to the insurance company for the particular prescription) and, in particular, how often and when adjudication may occur. For example, a rule may state that sufficient time should have elapsed after adjudication for the customer to consume some percentage of the prescribed day supply. This "minimum percent-fill consumed" could be stored as a record 194B in the database 182 or the database 146. Thus, for a medication prescribed with a 30-day supply, 23 days must elapse after the adjudication for the prescription if the adjudication rules for the particular insurance company (i.e., the minimum percent-fill consumed 194B) require that sufficient time elapse for the customer to consume 75% of the medication prior to adjudication the prescription again. The minimum percent-fill consumed 194B may vary based on the prescribed medication, the filling pharmacy, the third-party payor, the medical facility, the prescribed day supply, the customer, etc. Alternatively, or additionally, adjudication rules promulgated by a third-party payor may require that a minimum number of days elapse between two adjudications for a particular prescription. This information may be stored in a record 194A in the database 182 or the database 146. Such an "adjudication blackout period" 194A might, for example, require four, five, or even ten days between adjudications of a prescription. Another possible rule, promulgated by either a third-party payor or by a regulatory agency, may limit the amount of a medication (e.g., the number of tablets) dispensed to a customer by the pharmacy in a specific period of time.

Figure 2A:
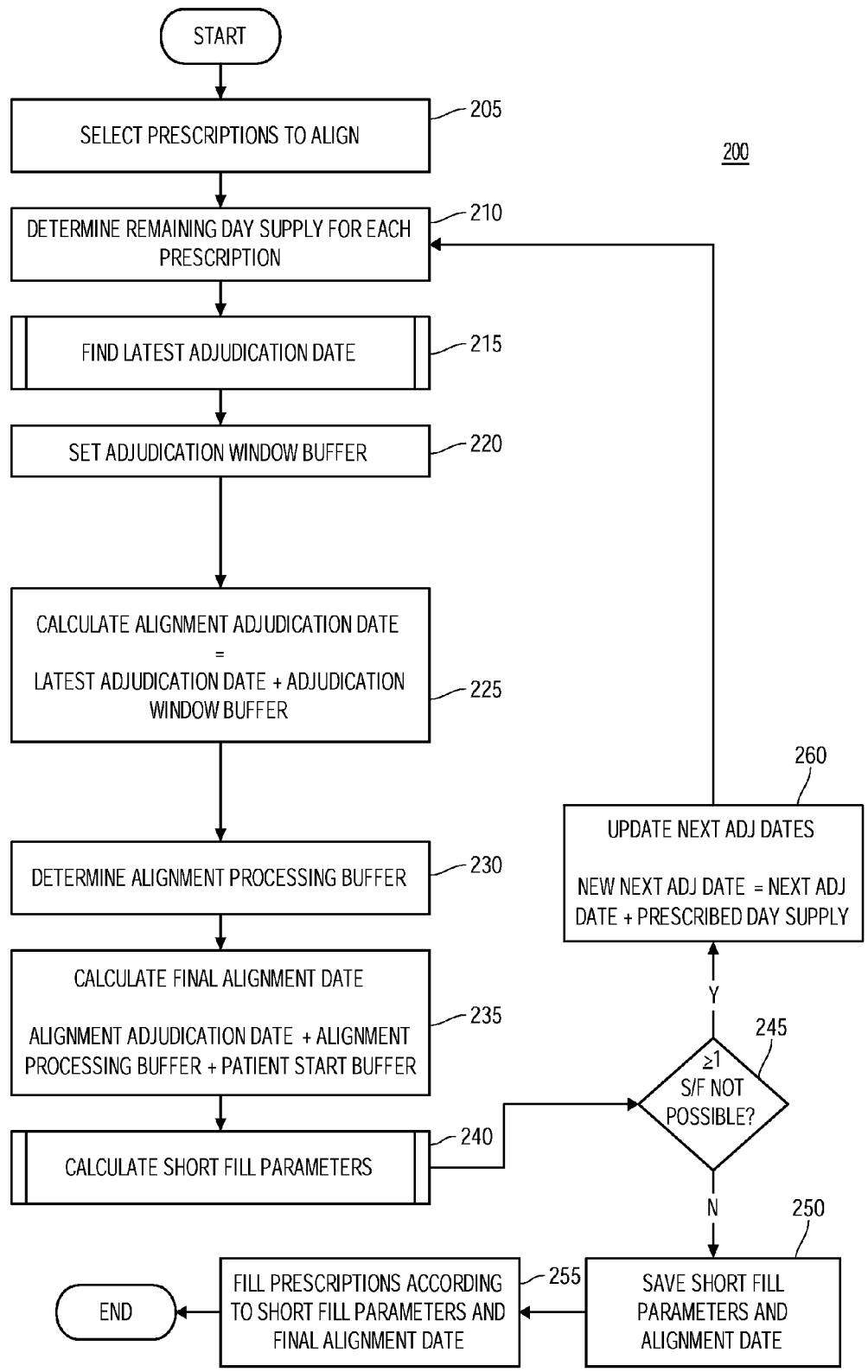
FIG. 2A illustrates an exemplary process for aligning the refill dates of a plurality of prescriptions to a calculated date in accordance with the described embodiments.

FIG. 2A illustrates an exemplary method 200 for efficiently aligning a plurality of prescription refill dates. The method 200 may begin when a user (e.g., the pharmacist, a call center operator, a customer accessing the service via the Internet, etc.) of the system 100 selects two or more prescriptions, which prescriptions' refill dates the customer wants aligned (block 205). The prescriptions selected in block 205 typically correspond to a single patient and a single customer record 192, and each selected prescription typically prescribes a maintenance medication (i.e., a medication taken regularly by the patient over an extended period of time). Of course, there is no reason that the selected prescriptions could not be for multiple patients (e.g., multiple patients under the care of a single caregiver, multiple family members, etc.) and it is conceivable that non-maintenance medications (including non-prescription medications) could be aligned with maintenance medications.

The system 100 determines the remaining day supply 196L for each of the selected prescriptions (i.e., how many days the remaining medication will last) (block 210). In some embodiments, the system 100 determines the remaining day supply 196L of each medication by calculating how much medication should remain, based on the last time the customer received a refill (or based on the last adjudication date 196J), the current date, and the prescribed day supply 196D. In other embodiments, the pharmacist asks the customer, for each selected prescription, how much of the medication remains. In any event, the system 100 may store the remaining day supply 196L with the prescription data 196 in the customer record 192. In most instances, the selected prescriptions will be prescriptions already filled by the customer at least once. However, it is possible for the selected prescriptions to include a newly-prescribed prescription. Where a newly-prescribed prescription is among the selected prescriptions, the remaining day supply 196L for that prescription may be the prescribed day supply 196D for that prescription if the prescription will be filled as prescribed. However, a newly-prescribed prescription may also be short-filled as part of the alignment process, in which case the remaining day supply 196L could be set to zero for the purposes of the short-fill calculations described below.

Of course, a newly-prescribed prescription could also be aligned with a plurality of already-aligned prescriptions. That is, two or more previously-aligned prescriptions could be selected in addition to one or more newly-prescribed prescriptions with the goal of aligning all of the selected prescriptions to the same date. Alignment of the prescriptions could be accomplished by aligning all of the prescriptions to a new date by treating the previously-aligned prescriptions as though they had not been previously aligned. Alternatively, alignment of the prescriptions could be accomplished by maintaining the alignment parameters of the previously-aligned prescriptions, and aligning the new prescription(s) to the same date as the previously-aligned prescriptions. Of course, a short fill (and possibly a full fill) may be required for the new prescription prior to alignment of the new prescription with those previously aligned.

In any event, having determined, at block 210, the remaining day supply 196L for each of the selected prescriptions, the system 100 proceeds to determine the next adjudication date 196K for each of the selected prescriptions, and then to determine the latest of those next adjudication dates among the selected prescriptions (block 215).

The latest of the next adjudication dates is the date on which a pharmacy could adjudicate all of the selected prescriptions and, in the absence of other considerations (e.g., adjudication blackout periods 194A related to short fills, discussed below), the latest of the next adjudication dates determined at block 215 would be the alignment adjudication date 197B (i.e., the date on which all of the prescriptions selected for alignment would be adjudicated). The customer would receive the selected prescriptions on the delivery date and would presumably consume the first of the medications one or more days after delivery (i.e., the final alignment date 197C).

Unless otherwise specified, the term "delivery," as used above and as used throughout this specification, refers to the customer's taking receipt of the prescribed medication(s). Thus, the prescribed medications may be delivered to the customer at the customer's home, work, or other provided address (e.g., where the medications are mailed, shipped, or couriered directly to the customer) or may be delivered to the customer at another location, such as a retail pharmacy 112 (e.g., where the medication is picked up by the customer). Throughout this specification, the terms "shipped," "shipping," and "ship" refer to any methods that may include a lead time including, but not limited to, mailing (e.g., via U.S. Post Office), shipping (e.g, via UPS or FedEx), etc.

Figure 3:
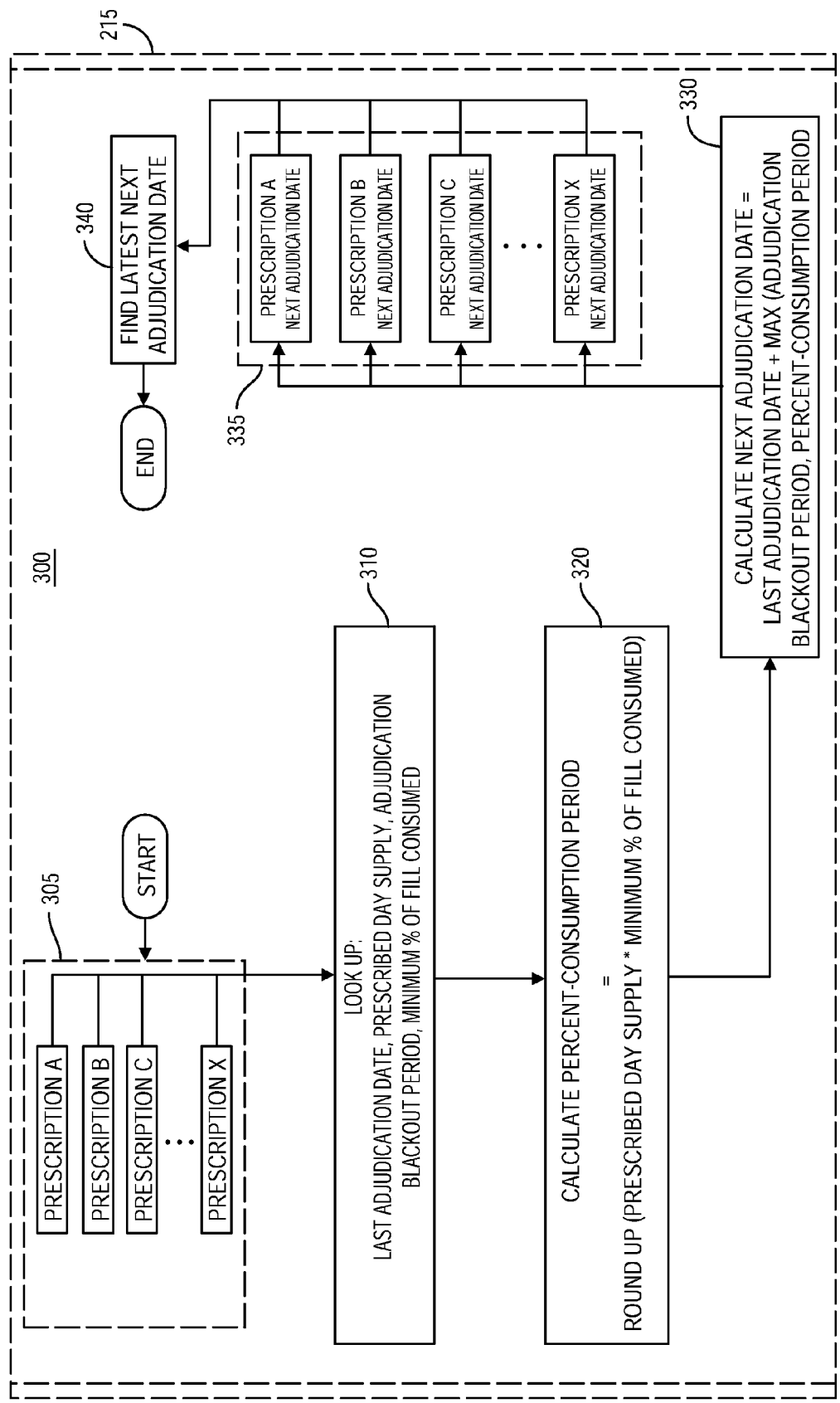
FIG. 3 illustrates an exemplary process for finding a latest adjudication date in accordance with the exemplary process illustrated in FIGS. 2A and 2B.

FIG. 3 illustrates an exemplary method 300 of finding the latest of the earliest next adjudication dates, the method 300 corresponding to the block 215 of FIG. 2A. The method 300 starts with the plurality of prescriptions selected for alignment. For each prescription, the system 100 retrieves various information (block 310). The information retrieved in the block 310 includes the last adjudication date 196J for the prescription, the prescribed day supply 196D for the prescription, the adjudication blackout period 194A, and the minimum percent-fill consumed 194B prior to the next adjudication. Of course, the system 100 may retrieve the various information from one or more customer records 192, or from various other records 194 or 199 in the database 146 or the database 182, and the information may be stored on, and retrieved from, a local storage location or a remote storage location (such as the database 146 or the database 182) accessed via the digital network 130 or the digital network 184. Moreover, the information retrieved in the block 310 may include more information or less information than described above. For example, an insurance company may not have an adjudication blackout period 194A, in which case the block 310 would not include retrieving the adjudication blackout period 194A.

Having retrieved the information in the block 310, the system 100 determines a percent-consumption period 196O (i.e., the number of days necessary for the customer to consume a required percentage of the current fill for the prescription, assuming, of course, that the customer does not skip any doses) (block 320). The block 320 illustrated in FIG. 3 shows one method of determining the percent-consumption period 196O. The number of days it takes to consume the required minimum percent-fill consumed 194B of the fill for the prescription determines the percent-consumption period 196O. For example, suppose a prescription prescribes a 30-day supply of a medication, and that a third-party payor requires that sufficient time elapse for the customer to consume 77% of the prescription before adjudicating the prescription for refill. 77% of 30 days is 23.1 days (i.e., 30*0.77=23.1). Rounding up, 24 days must elapse for the customer to have consumed 77% of the medication. In this case, the percent-consumption period 196O is 24 days. In some cases, the rules may allow rounding down, in which case 23 days must elapse for the customer to have consumed 77% of the medication.

As described above, the various rules that third-parties promulgate may include not only a minimum percent-fill consumed 194B, but may also include an "adjudication blackout period" 194A (i.e., a rule requiring a minimum period of time between adjudications of a prescription). The larger of the adjudication blackout period 194A and the percent-consumption period 196O will determine the next adjudication date 196K for the prescription. The system 100 calculates the next adjudication date 196K for the prescription using the last adjudication date 196J and the larger of the adjudication blackout period 194A and the percent-consumption period 196O (block 330). Using the method 300, the system 100 calculates the next adjudication date 196K for the prescription by adding the larger of the adjudication blackout period 194A and the percent-consumption period 196O (determined at block 320) to the last adjudication date 196J. Continuing with the example above, if the last adjudication date 196J for a prescription is July 1, the adjudication blackout period 194A is 6 days, and the percent-consumption period 196O, determined at block 320, is 24 days, the next adjudication date 196K on which adjudication for the prescription may occur is July 25 (24 days after the last adjudication on July 1).

When the system 100 has performed the operations illustrated in blocks 310 through 330 for each of the prescriptions, each of the prescriptions will have associated with the corresponding data 196 a next adjudication date 196K (block 335). The system 100 then selects the latest of the next adjudication dates 196K (block 340). Thus, if the next adjudication dates 196K for three prescriptions were July 13, July 17, and July 20, the system 100 would select July 20 as the latest adjudication date.

Of course, in some instances, such as where a customer does not have insurance coverage for medication or where none of the medications are covered by a customer's insurance (e.g., the dispensed medications are all vitamins), there may be no rules applicable to the dispensed medications at all. In these instances, the adjudication rules (e.g., the adjudication blackout period 194A or the minimum percent-fill consumed 194B) may be set to zero, or the blocks calculating associated parameters (e.g., the block 320) may be omitted entirely. In other instances, such as when the pharmacy does not charge the customer for a short fill or when the customer pays cash for a short fill instead of billing his or her insurance company, the adjudication rules (e.g., the adjudication blackout period 194A or the minimum percent-fill consumed 194B) may be set to zero for the short fills (or the associated blocks omitted), but adjudication rules would still apply to the non-short-fill deliveries of medication. In still other instances, the system 100 may determine that one or more prescriptions requiring a short fill would, if the short fill were adjudicated, cause the final alignment date to be delayed (e.g., where the next adjudication date after the short fill adjudication would not provide sufficient time to deliver to the aligned medications to the customer before the calculated or selected alignment date). In these instances, the system 100 may select the prescription (or prescriptions, if there are more than one prescription, the short fill of which would delay the alignment date) and avoid the adjudication of the prescription (e.g., by providing the short fill to the customer for free, by charging the customer cash, etc.).

In some instances, though, the customer will exhaust his or her supply of one or more of the medications prescribed by the selected prescriptions prior to the latest adjudication date determined at block 215 or, in any event, prior to the final alignment date 197C. In such an instance, the customer will require a refill of one or more of the selected medications before the final alignment date 197C in order to avoid missing any doses and may receive a short fill that contains less than the prescribed day supply 196D of the medication. Of course, filling the prescription, even with a short fill, may restart the adjudication period for that prescription and create a post short-fill next adjudication date 198C for that prescription. In some cases (e.g., where the pharmacy does not charge the customer for the short fill or where the customer pays cash for the short fill instead of billing an insurance company), adjudication rules would not apply and, therefore, the adjudication period would not restart. In other cases, the post short-fill next adjudication date 198C (i.e., the next adjudication date after the short fill) may not fall until after the latest adjudication date determined at block 215 (i.e., a post short-fill next adjudication date 198C will be after the latest adjudication date).

Referring again to FIG. 2A, the system 100, employing method 200, then addresses situations where the latest adjudication date determined at block 215 requires one or more short fills, which short fills may cause post short-fill next adjudication dates 198C for the short-filled prescriptions to fall after the latest adjudication date (block 220). In some embodiments, the method 200 addresses this situation simply by determining an adjudication window buffer 193B sufficient to ensure that all of the selected prescriptions may be adjudicated at some common point subsequent to the latest adjudication date determined at block 215. For example, the adjudication window buffer 193B may be set to three days, four days, five days, etc. In this manner, the adjudication window buffer 193B allows sufficient time to elapse, after adjudication of a prescription for the purpose of a short fill, so that the prescription may be adjudicated again on whatever date is selected as the final alignment date. In other embodiments employing method 200, the adjudication window buffer 193B may not be utilized, in which case it may be set to zero days or the step may be excluded.

Using method 200, the system 100 next determines an alignment adjudication date 197B (block 225). The alignment adjudication date 197B is the date on which the system 100 will adjudicate all of the selected prescriptions for the final alignment. In an embodiment employing a simple adjudication window buffer 193B, the method 200 includes calculating the alignment adjudication date 197B by adding the adjudication window buffer 193B determined at block 220 to the latest adjudication date determined block 215.

Regardless of the method by which the system 100 determines the alignment adjudication date 197B, the alignment adjudication date 197B is the date on which all of the selected prescriptions may be adjudicated and is not necessarily the final alignment date 197C. This is because additional time related to the processing of the prescription may further delay the date on which the customer receives the prescribed medication. Adjudication of the prescription, filling the prescription, shipping the prescribed medication, and delivery time may all delay the date on which the customer receives the prescribed medication. For example, if the adjudication process takes place near the end of the business day, it may be too late to ship the prescribed medications, even if the pharmacy 112 or the central-filling facility 114 fills the prescriptions on the same day as adjudication. Once the pharmacy 112 or the central-filling facility 114 ships the selected prescriptions, the shipping process could take anywhere from one day to five days or more, depending on the carrier, the relative locations of the pharmacy 112 and the customer, the weather, and various other factors. Moreover, additional processes, such as printing blister packages for aligned prescription medications, may extend the time elapsing between adjudication of the prescription by the pharmacy 112 and delivery to the customer.

Alternatively, "delivery" of the prescriptions to the customer could be accomplished in person (i.e., the customer could pick the prescriptions up at a retail pharmacy). Thus, while some embodiments described herein contemplate delivery of prescriptions to the customer by some form of shipping or courier service, the term "deliver," as used within this application, means to provide the medication to the customer. For example, the prescription alignment system 100 contemplated herein could also "deliver" prescriptions to a customer when the customer comes to the pharmacy to pick up the prescriptions. In such instances, various blocks of method 200 may be modified or omitted where necessary. Some of the necessary modifications and/or omissions are indicated, where appropriate, in the following paragraphs.

The system 100 then determines an alignment processing buffer 193A, which accounts for the time consumed by the various events occurring between the alignment adjudication date 197B and the final alignment date 197C (block 230). For example, the system 100 (or the person or persons programming the system 100) may allot one day for adjudication of the prescription and printing of a blister pack, one day for filling and shipping the selected prescriptions to the customer, and two days for delivery. Or, for example, the system 100 may allot one day for adjudication of the prescription and printing of a blister pack, one day for filling and shipping the selected prescriptions to a retail pharmacy 112, and two days for delivery to the customer (i.e., two days for the customer to pick up the prescription from the retail pharmacy 112). If desired, the system 100 may add additional time (e.g., one day, two days, etc.) as a buffer, to account for unexpected transportation delays and the like. Of course, each of these numbers may be any number selected to reflect the processes utilized in the particular system 100. Thus, the alignment processing buffer 193A is a variable and may be set depending on the patient, the prescription, the order, or other factors such as the method of delivery. For example, if the prescriptions are filled and delivered to the customer at a retail pharmacy 112 (i.e., if the customer picks up the prescriptions) the alignment processing buffer 193A would not include time for shipping, but may account for delays by the customer in stopping at the retail pharmacy 112 to pick up the prescriptions. Alternatively, if the prescriptions are filled at a central-filling facility 114 and shipped to the pharmacy 112 for the customer to pick up, the alignment processing buffer 193A could include the time for shipping. Some embodiments may require retrieving the alignment processing buffer 193A from a storage location, such as the database 146 or the database 182 at the block 230. Still other embodiments are envisioned which omit the block 230 entirely, such as, for example, embodiments in which the selected prescriptions are adjudicated, filled, and delivered to the customer in a single day, for example by filling the prescriptions at a retail pharmacy 112 and having the customer pick up the prescriptions or by delivering the prescriptions by courier.

The system 100 next determines the final alignment date 197C (block 235). The final alignment date 197C is the alignment adjudication date 197B determined at block 225, incremented by the alignment processing buffer 193A (determined at block 230) and by a patient start buffer 193D. The patient start buffer 193D allows one or more days for the patient to begin consuming the medication. For example, in one embodiment, the patient start buffer 193D is one day. The additional day accounts for the fact that the customer will likely not start consuming the medication until the day following delivery (by retail pick-up or shipping receipt) of the prescriptions. Of course, the additional day is not required and some embodiments may choose to set the final alignment date 197C to the alignment adjudication date 197B incremented by the alignment processing buffer 193A, omitting the extra day.

Figure 2B:
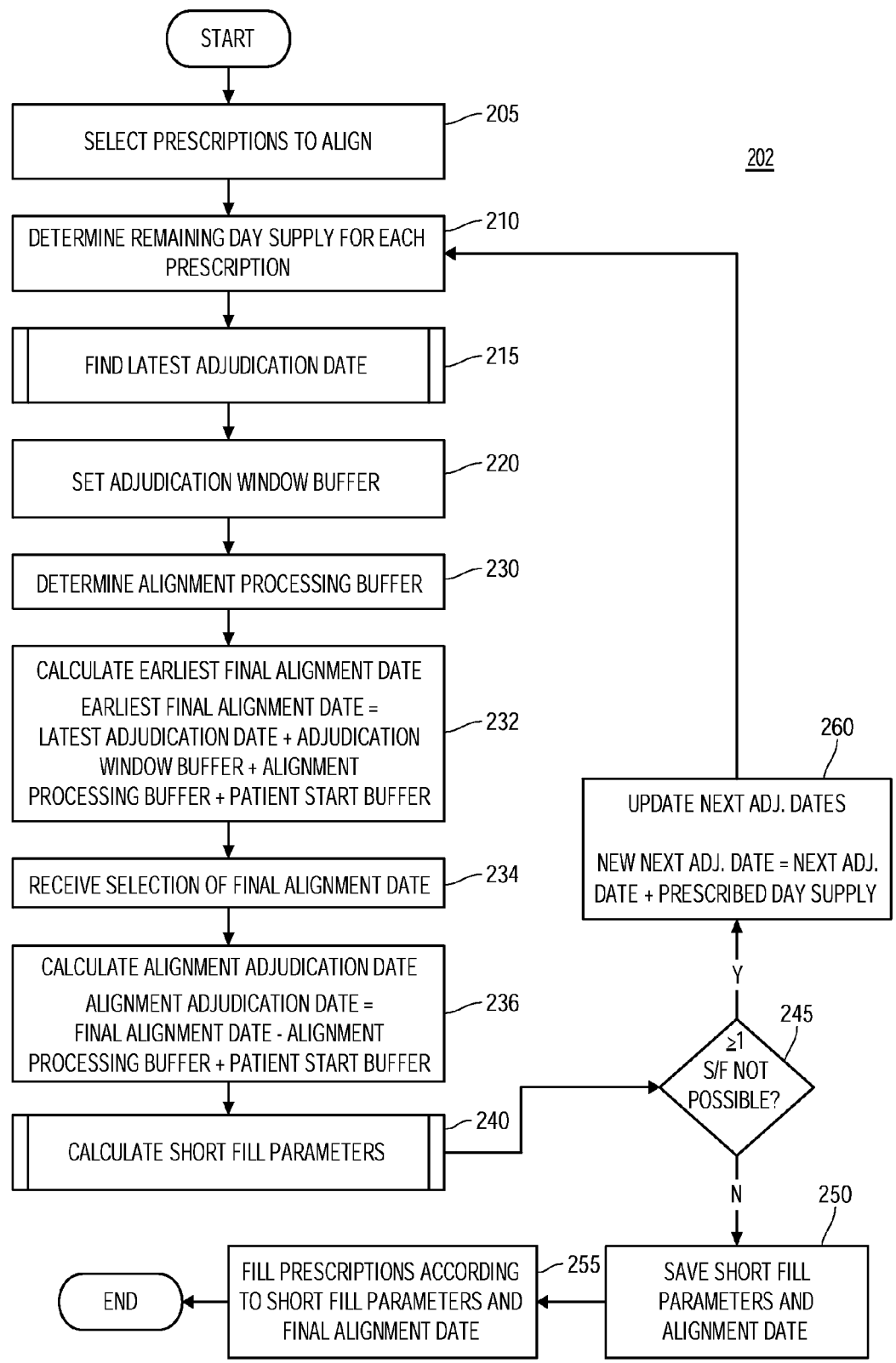
FIG. 2B illustrates an exemplary process for aligning the refill dates of a plurality of prescriptions to an arbitrary date, in accordance with the described embodiments.

Of course, the final alignment date 197C could also be chosen arbitrarily. For example, a customer may choose to align a plurality of prescriptions such that the alignment or adjudication dates for the prescriptions fall on, around, or after a certain day of the month (e.g., after they get paid, on a day on which they have a personal assistant, etc.). FIG. 2B illustrates a method 202 for aligning the plurality of prescriptions to an arbitrary date, rather than to a calculated date, as accomplished by the method 200 depicted in FIG. 2A. The system 100 initiates the method 202 in the same manner as the system 100 initiates the method 200, and proceeds, in the same manner as in the method 200, to select prescriptions to align (block 205), determine the day supply remaining 196D for each prescription (block 210), find the latest adjudication date for each prescription (block 215), and set the adjudication window buffer 193B (block 220).

However, after setting the adjudication window buffer 193B (block 220), the system 100 proceeds in method 202 to determine the alignment processing buffer 193A (block 230). Once the system 100 determines both the alignment processing buffer 193A and the adjudication window buffer 193B, the system 100 calculates the earliest final alignment date that the customer (or other user of the system 100) may select. The system 100 calculates the earliest final alignment date by adding to the latest adjudication date (determined at the block 215) a number of days equivalent to the sum of the adjudication window buffer 193B, the alignment processing buffer 193A, and the patient start buffer 193D (block 232). For example, if the latest adjudication date for a plurality of selected prescriptions were August 19, and the alignment processing buffer 193A, adjudication window buffer 193B, and patient start buffer 193D, were three days, five days, and one day, respectively, the earliest final alignment date that a customer or user could select would be August 28. Of course, circumstances may exist in which any of the various buffers 193A, 193B, 193D, etc. may be set to zero.

After determining the earliest final alignment date (block 232), the system 100 receives a selection of a final alignment date 197C (block 234). The final alignment date 197C must be on or after the earliest final alignment date (determined at block 232). Once the system 100 has received the selection of a final alignment date 197C (block 234), the system 100 calculates the alignment adjudication date 197B (block 236) that will result in the selected final alignment date 197C. The system 100 calculates the alignment adjudication date 197B by subtracting from the selected final alignment date 197C (received at block 234) a number of days equal to the alignment processing buffer 193A plus the patient start buffer 193D.

Figure 4:
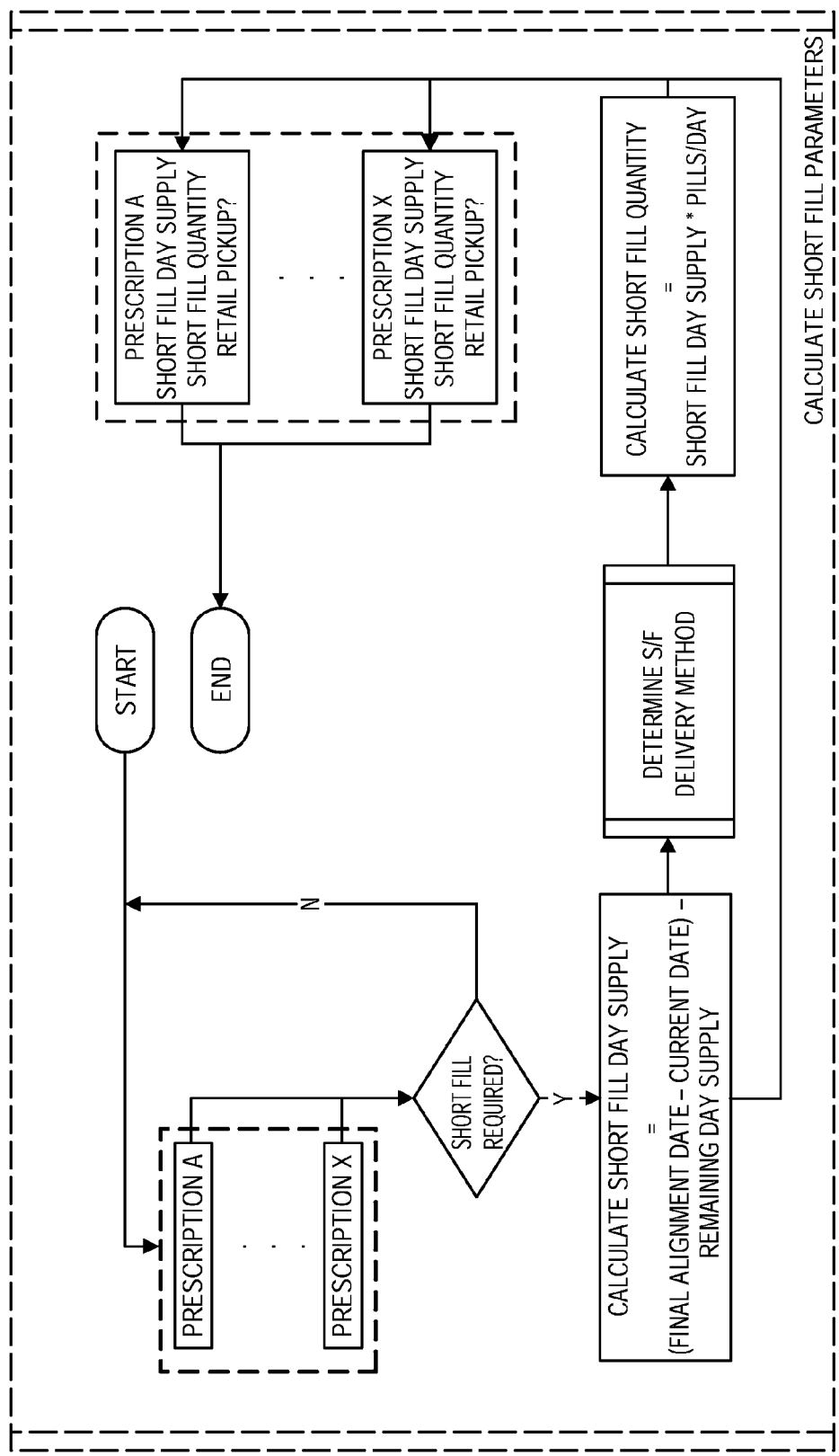
FIG. 4 illustrates an exemplary process for calculating a plurality of short-fill parameters in accordance with the exemplary process illustrated in FIGS. 2A and 2B.

In any event, after the system 100 determines the final alignment date 197C at block 235 of the method 200 (or at blocks 232-236 of the method 202), the system 100 calculates the parameters of any required short fills (block 240). FIG. 4 illustrates a method 400, corresponding to block 240 of the methods 200 and 202, for determining the parameters of any short fills. The method 400 starts with the plurality of selected prescriptions. The method 400 determines, for each of the selected prescriptions, whether the prescription requires a short fill in order for the customer to have sufficient medication to last until the final alignment date 197C without skipping or missing any doses (block 405). To determine whether a short fill is required for a selected prescription, the system 100 determines, based on the remaining day supply 196L, whether the customer has sufficient medication to last until the final alignment date 197C. For each prescription that does require a short fill, the system 100 calculates a short-fill day-supply 198D for the prescription (i.e., how many days of medication must be supplied to provide the customer with sufficient medication to get to the final alignment date 197C) (block 410). The system 100 determines the short-fill day-supply 198D for the prescription by finding the difference between the remaining day supply 196L (determined at block 210 of the method 200) and the number of days between the final alignment date 197C (determined at block 235 of the method 200) and the current date. For example, if the final alignment date 197C is July 28, and the current date is July 14, the number of days between the final alignment date 197C and the current date is 14. If the method 200 determined that the customer has six days of medication left at block 210, the short-fill day-supply 198D for the prescription, calculated by the method 200 at block 410, would be eight days.

Next, the system 100 determines whether a short-fill is possible and, if so, determines a short-fill delivery method 198H and the short-fill delivery date 198F for the prescription (block 415). The details of these determinations are described below with reference to FIG. 5. In any event, if the system determines at block 415 that a short fill is possible, the system 100 calculates the short-fill quantity 198E (i.e., the number of pills to dispense in the short-fill) by multiplying the short-fill day-supply 198D for the prescription (determined at block 410) by the prescribed dose (e.g., how many pills/day) 196C for the prescription (block 470). The results of the calculations and determinations performed at blocks 410, 415, and 470 are associated with each of the prescriptions.

Figure 5:
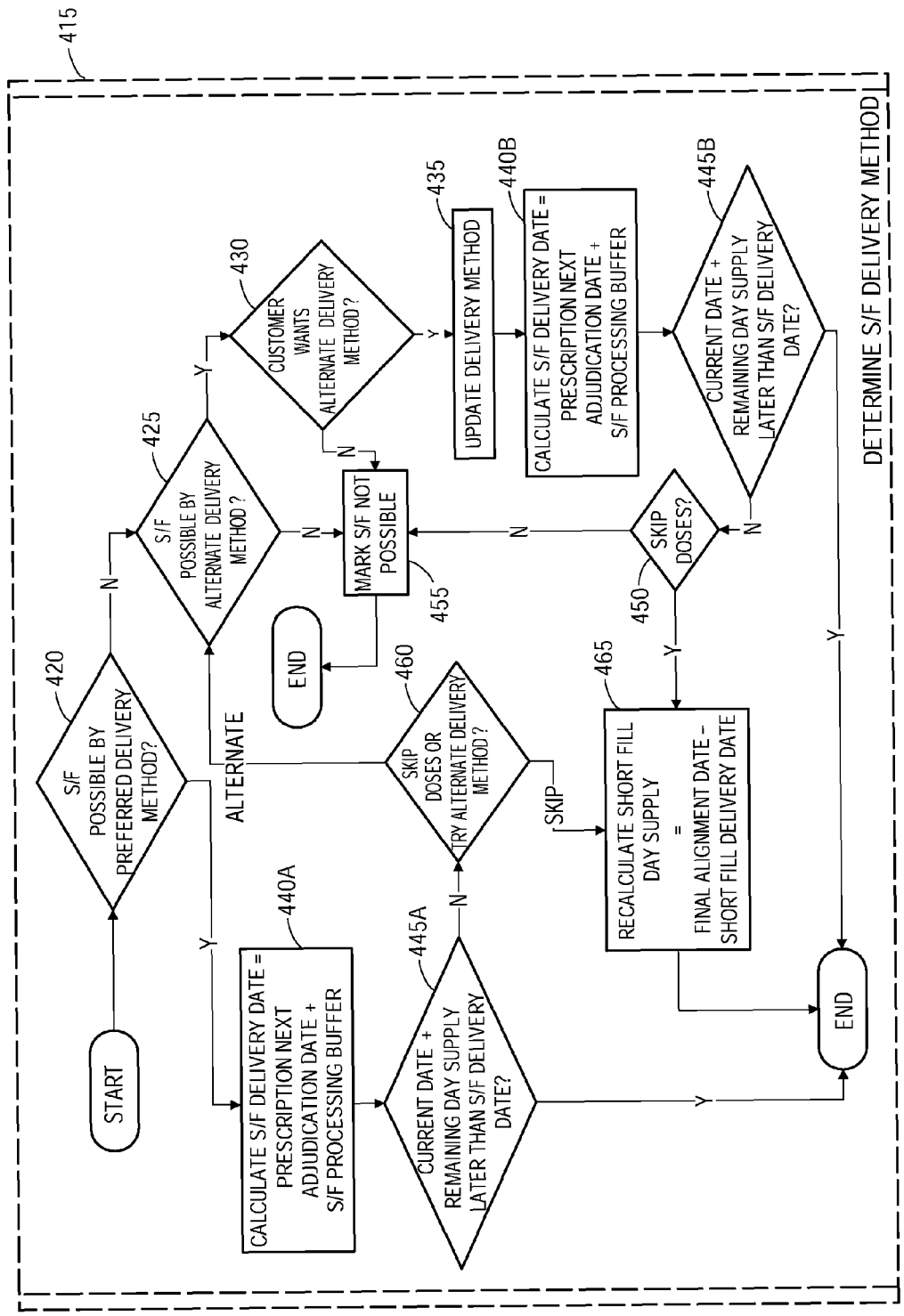
FIG. 5 illustrates an exemplary process for determining a short-fill delivery method in accordance with the exemplary process illustrated in FIG. 4.

FIG. 5 depicts the block 415 in greater detail. The system 100 retrieves the customer's preferred delivery method 195G stored in the customer profile 195, and determines whether the preferred delivery method (e.g., store pick-up, shipped to customer, etc.) can accommodate a short-fill for the medication (block 420). If the customer's preferred delivery method can accommodate a short-fill for the medication, the system 100 calculates the short-fill delivery date 198F for that method by adding to the next adjudication date 196K for the prescription, the number of days indicated by the short-fill processing buffer 193C (block 440A). The short-fill processing buffer 193C may, in some embodiments, be dependent on the particular delivery method employed, the patient, the prescription, the order, or any number of other factors. For example, the short-fill processing buffer may be longer if the delivery method includes shipping a prescription from a warehouse or a central-filling facility to a customer or to the pharmacy than it would be if the delivery method includes filling the prescription at a local store and having the customer pick it up from the store.

After calculating the short-fill delivery date 198F (at block 440A) the system 100 determines, based on the short-fill delivery date 198F, whether the customer can receive the short fill before exhausting the supply of medication (block 445A). If the short-fill delivery date 198F indicates that the medication will arrive before the customer exhausts his or her supply of medication (as indicated by the remaining day supply 196L) (i.e., if the current date incremented by the remaining day supply 196L is later than the short-fill delivery date 198F), then the system 100 stores the information and proceeds to calculate the short-fill quantity (block 470). If, on the other hand, the short-fill delivery date 198F indicates that the medication will not arrive before the customer exhausts his or her supply of medication, the system 100 (or a pharmacist acting in accordance with the system 100) may inquire as to whether the customer prefers to skip doses and take delivery using the preferred method or try an alternative method (block 460). For example, if the customer's preferred delivery method 195G is shipping, but shipping the short fill of the prescribed medication to the customer would result in the short fill arriving after the customer has exhausted the remaining day supply 196L, the customer may be asked if he or she can take delivery of the short fill at a retail pharmacy location 112.

If the customer prefers to take delivery using the preferred method, even if this means skipping doses, the system 100 recalculates the short-fill day supply 198D by finding the difference between the final alignment date 197C and the short-fill delivery date 198F (block 465). If, on the other hand, the customer indicates at the block 460 a preference to try an alternative method for delivery or if, at the block 420, short-fill is not possible using the preferred delivery method, the system 100 evaluates whether the short-fill is possible using an alternate delivery method (block 425). If the short-fill is not possible by an alternate delivery method, the system 100 creates an indication 198G that the short-fill is not possible (block 455). Likewise, if the short-fill is possible using an alternate delivery method (block 425) but the customer refuses the alternate delivery method (block 430), the system 100 creates an indication 198G that the short-fill is not possible (block 455).

If the short-fill is possible by an alternate delivery method (block 425) and the customer wants to accept delivery via the alternate method (block 430), the system 100 updates a short-fill delivery method 198H (which would otherwise be the same as the customer's preferred delivery method 195G) for the prescription (block 435). Next, the system 100 calculates the short-fill delivery date 198F for the alternate delivery method by adding to the next adjudication date 196K for the prescription, the number of days indicated by the short-fill processing buffer 193C (block 440B). Of course, the short-fill processing buffer 193C may be different for the alternate delivery method than for the preferred delivery method.

After calculating the short-fill delivery date 198F for the alternate delivery method (at block 440B), the system 100 determines, based on the short-fill delivery date 198F, whether the customer can receive the short fill before exhausting his or her supply of medication (block 445B). If the short-fill delivery date 198F indicates that the medication will arrive before the customer exhausts the supply of medication (as indicated by the remaining day supply 196L) (i.e., if the current date incremented by the remaining day supply 196L is later than the short-fill delivery date 198F), then the system 100 stores the information and proceeds to calculate the short-fill quantity (block 470). If, on the other hand, the short-fill delivery date 198F indicates that the medication will not arrive before the customer exhausts the supply of medication, the system 100 (or a pharmacist acting in accordance with the system 100) may inquire as to whether the customer prefers to skip doses, taking delivery using either the preferred or alternate method (preferably the method resulting in the least number of missed doses), or recalculate the final alignment (block 450). If the customer prefers to skip doses, the system 100 recalculates the short-fill day supply 198D by finding the difference between the final alignment date 197C and the short-fill delivery date 198F (block 465). If, on the other hand, the customer does not want to skip any doses, the system 100 creates the indication 198G that a short fill is not possible for the prescription (block 455).

Of course, the system 100 need not, in all embodiments, offer an alternate delivery method or the opportunity to skip doses. In one embodiment, if the short-fill is not possible by the preferred delivery method, or if the short fill will not be delivered to the customer before the customer exhausts the supply of medication, the system 100 creates the indication 198G that the short-fill is not possible. In another embodiment, the system 100 automatically attempts to fulfill a short fill by an alternate delivery method if the preferred method would result in the customer exhausting the supply of the medication before the short fill could be delivered by the customer's preferred method. Additionally, the system 100 may, in some embodiments, offer multiple alternate delivery methods. In such embodiments, the system may proceed, after determining that one alternate delivery method is not possible (block 425) or determining that the customer does not want the alternate delivery method (block 430) or determining that the customer does not want to skip doses (block 450), to try an additional alternate delivery method by determining whether delivery of the short fill is possible using yet another alternate delivery method (block 425). Where there are multiple alternate delivery methods available, the system 100, in one embodiment, gives the patient the option of prioritizing the alternate delivery methods or, in any event, indicating a preference for one over another. In another embodiment, the system 100 prioritizes the alternate delivery methods.

In any event, after the system 100 calculates a short-fill delivery date 198F and possibly a recalculated short-fill day supply 198D (block 415), the system calculates a short-fill quantity 198E as described above (block 470). If, at block 415, the system 100 determines that the short-fill is not possible (indication 198G), the system 100 may skip the step of calculating the short-fill quantity 198E.

Referring once again to FIG. 2A, after calculating the short-fill parameters (block 240) the system 100 determines whether the records 198 for any of the prescriptions contain an indication 198G that the short-fill is not possible for that prescription (block 245). If none of the prescriptions are marked indicating that the short-fill is not possible, the system 100 saves the short-fill parameters 198B-198H calculated at block 240 and the final alignment date 197C calculated at block 235 (block 250). The system 100 directs the pharmacist to fill the prescriptions in accordance with the short fill parameters 198B-198H and the final alignment date 197C (block 255).

If the system 100 determines, at block 245, that the records 198 for one or more of the prescriptions contain an indication 198G that the short fill is not possible, control passes to a block 260. As described above, a record 198 may include an indication 198G that a prescription cannot be short-filled because the preferred method of delivery cannot accommodate short fills or because a short fill with the preferred method will not arrive before the patient exhausts the supply of the medication. There could be other reasons why a short fill is not possible as well. For example, a particular third-party payor may not allow short fills, or the filling pharmacy (or warehouse or central filling location) may be temporarily out of stock of the medication. Whatever the reason, when a prescription record 198 indicates that a short-fill is not possible, the pharmacy will dispense the prescribed day supply 196D for the prescription. Of course, this means that the system 100 must recalculate the parameters calculated for the alignment process in the previous blocks of the method 200. Thus, in one embodiment, at block 260 the system 100 updates the next adjudication dates 196K for each of the prescriptions by adding the prescribed day supply 196D for the prescription to the next adjudication date 196K for the prescription (determined at block 315 of the method 300), and control passes back to the block 210. The system 100 proceeds through the blocks 210-255 using the updated information. In this embodiment, the system need only proceed through the blocks 210-255 one additional time. However, in an alternate embodiment, the system 100 updates the next adjudication date 196K for the prescription for which a short fill is not possible by adding the prescribed day supply 196D for the prescription to the next adjudication date 196K for the prescription. The system 100 then proceeds through the blocks 210-255, repeating the process if a short fill is not possible for another of the prescriptions.

In one embodiment, delivery of prescriptions using the alignment system 100 occurs primarily by shipping the medications directly to the customer from one of the retail locations 112 or from a warehouse or central-filling facility 114, and the retail locations 112 may also deliver short fills related to prescription alignment to the customer by having the customer pick up the short fills of medication. This allows a customer to receive a short fill of a prescribed medication even where the short-fill delivery date 198F for the primary delivery method (i.e., shipping the prescription to the customer) is later than the next adjudication date 196K for the prescription. In such an embodiment, the method 200 may omit blocks 245 and 260, as there may be no reason to evaluate whether any of the short fill prescription records 198 include an indication 198G that the short fill is not possible, and no reason to update the next adjudication dates 196K for the prescriptions. Where blocks 245 and 260 are omitted, control passes directly from the block 240 to the block 255, at which block the prescriptions requiring short fills are filled according to the short fill parameters 198B-198H, and all of the selected prescriptions are filled according to the final alignment date 197C.

In other alternate embodiments, there are no rules limiting the adjudication of the selected prescriptions (i.e., the adjudication blackout period 194A and the percent-consumption period 196O are each zero). In these embodiments, the system 100 calculates the next adjudication date 196K for each of the prescriptions at block 330, and then determines the latest adjudication date among the selected prescriptions (at block 340). Of course, if the adjudication blackout period 194A and the percent-consumption period 196O are each zero, then the next adjudication date 196K may be any date, and in such a case the next adjudication date 196K may be calculated using other information. For example, the next adjudication date 196K may be calculated by determining when the customer will next need a refill of the medication. In any event, the latest adjudication date 196K among the selected prescriptions is the alignment adjudication date 197B, and the pharmacy 112 begins the process of adjudicating, filling, and shipping (or otherwise delivering) the prescription a number of days before the final alignment date 197C. The number of days is preferably the same as the alignment processing buffer 193A.

In yet other embodiments, the pharmacy may provide overfills of one or more medications in order to align the refill dates of the selected prescriptions. For example, if a calculated final alignment date for a group of selected prescriptions is far enough in the future, aligning the refill dates of the selected prescriptions may require one or more full fills of one or more of the other selected prescriptions, in addition to one or more short fills of the one or more of the other selected prescriptions. This would be the case where, for example, one of the selected prescriptions was recently filled with a 90-day supply, and the others of the selected prescriptions are each for 30-day supplies. Thus, as an alternative to providing one or more 30-day full fills and possibly a short fill for each of the selected prescriptions that has a 30-day supply, the pharmacy could provide an overfill for each of the prescriptions having the shorter prescribed day supply. An overfill may also be utilized to achieve the same result as the adjudication window buffer 193B.

In some instances, the number of prescriptions selected for alignment and the timing of the various refills for the prescriptions may be such that the aligning all of the prescriptions would mandate a final alignment date that is at a relatively later date than desired. However, it may be possible that an earlier alignment date could be achieved while still accommodating alignment of a relatively high percentage (e.g., 90%) of the selected prescriptions, and then adding the remaining non-aligned prescriptions (e.g., the remaining 10%) to the alignment at a later date.

Figure 6:
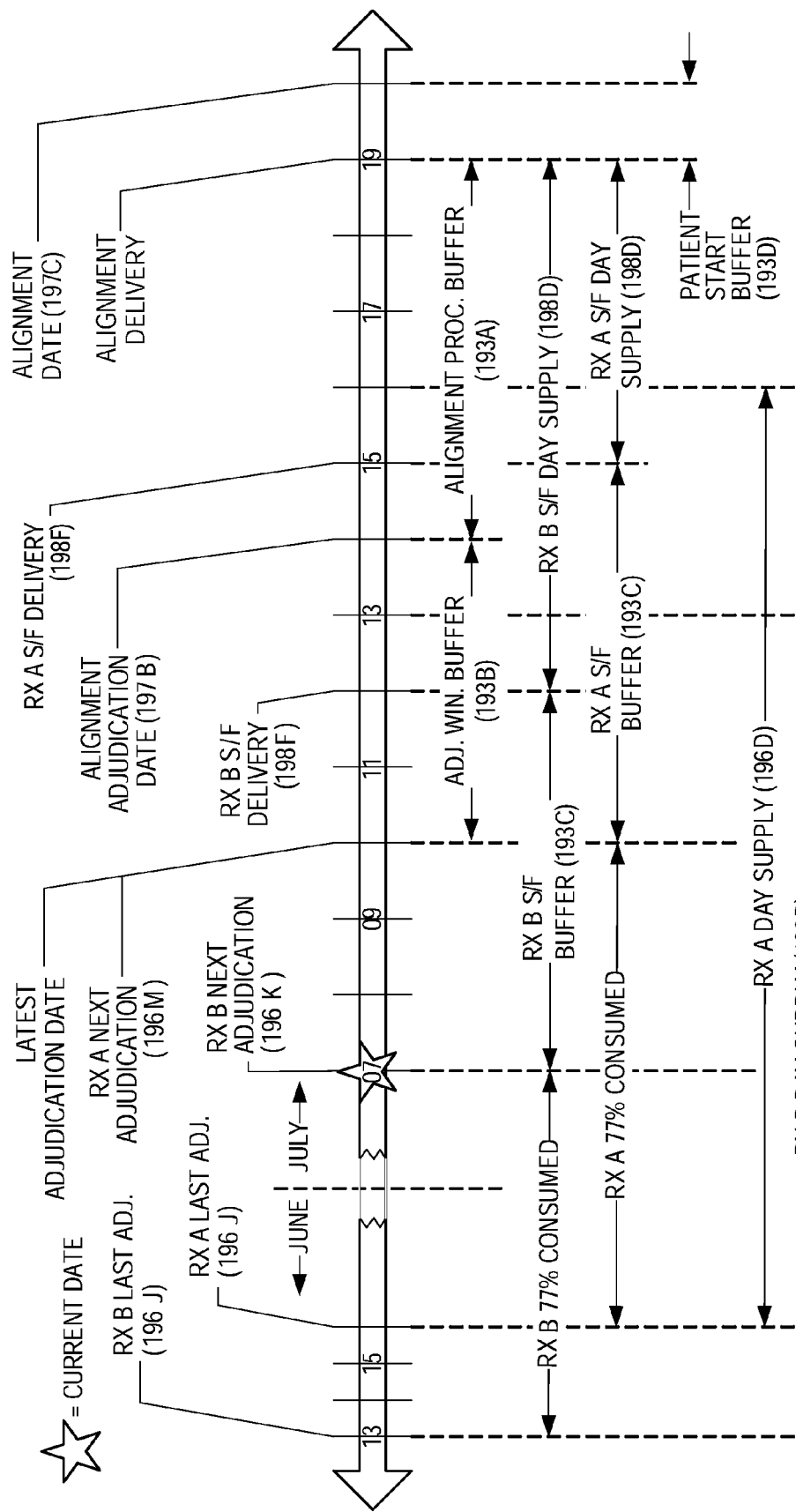
FIG. 6 depicts a timeline illustrating the exemplary alignment of two prescriptions in accordance with the described embodiments.

FIG. 6 depicts a timeline illustrating the exemplary alignment of two prescriptions in accordance with one embodiment described above. The timeline extends from June 13 of an arbitrary year to July 20 of the same year, and illustrates the various dates and periods associated with alignment of the two prescriptions, prescription A (depicted as "RX A") and prescription B (depicted as "RX B"), each of the prescriptions A and B having a 30-day prescribed day supply 196D. July 7 is the current date, as indicated on the timeline. The illustrated example assumes an adjudication blackout period 194A of four days, and a minimum percent-fill consumed 194B of 77%.

Alignment of the prescriptions A and B proceeds with reference to the methods 200, 300, and 400, depicted in FIGS. 2, 3, and 4 and 5, respectively. Having selected the prescriptions A and B for alignment (at block 205), the system 100 determines the remaining day supply 196L for each prescription (at block 210) by finding the difference between the current date (July 7) and the last adjudication date 196J for the prescription. The timeline depicts that prescription A has a last adjudication date 196J of June 16 ("RX A Last Adjudication") and prescription B has a last adjudication date 196J of June 13 ("RX B Last Adjudication"). On July 7, then, prescriptions A and B would have nine and six days of medication remaining, respectively (assuming that the last adjudication occurred on the same day as the last delivery and that the patient consumed the first dose on the same day (i.e, that the patient start buffer was zero)).

The system 100 proceeds to find the latest adjudication date (at block 215) for the two prescriptions A and B using the method 300. For each prescription, the system 100 looks up the last adjudication date 196J, the prescribed day supply 196D, the adjudication blackout period 194A (if there is one), and the minimum percent of the fill that must be consumed 194B (if there is one) (at block 310). Table 1, below, summarizes the results of the method 300 at block 310.

TABLE 1

|  | RX A | RX B |
|---|---|---|
| Last Adjudication Date (196J) | June 16 | June 13 |
| Prescribed Day Supply (196D) | 30 | 30 |
| Adjudication Blackout Period (194A) |  | 4 days |
| Minimum Percent-Fill Consumed (194B) |  | 77% |

FIG. 6 illustrates the last adjudication dates 196J for each of the two prescriptions A and B and the prescribed day supply 196D for each of the two prescriptions A and B.

The system 100 uses the information retrieved above at block 310 and, in particular, the prescribed day supply 196D and the minimum-percent fill consumed 194B, to calculate the percent-consumption period 196O (block 320). The system 100 calculates the percent-consumption period 196O by multiplying the prescribed day supply 196D by the minimum-percent fill consumed 194B, and in this case rounding up to the next whole number. Of course, in the example depicted in FIG. 6, the percent-consumption periods 196O for the Prescriptions A and B are the same—24 days. FIG. 6 illustrates the period between the last adjudication date (which is assumed in this example to also be the same day that the customer started taking the medication) and when the minimum-percent fill consumed 194B is reached for each prescription ("RX A/B 77% Consumed").

After determining the percent-consumption periods 196O, the system 100 calculates the next adjudication date 196K for each prescription (at block 330) by incrementing the last adjudication date 196J by the larger of the adjudication blackout period 194A and the percent-consumption period 196O for the prescription. In the example depicted in FIG. 6, the next adjudication dates 196K for the Prescriptions A and B are July 10 and July 7, respectively (i.e., the respective last adjudication dates 196J incremented by 24 (the larger of the adjudication blackout period 194A (four days) and the percent-consumption period 196O (24 days)). The timeline depicted in FIG. 6 illustrates the next adjudication dates 196K for each of the prescriptions A and B ("RX A/B Next Adjudication"). From the next adjudication dates 196K for each of the prescriptions A and B—July 10 and July 7, respectively— the system selects the latest adjudication date ("Latest Adjudication Date") (at block 340, to complete block 215).

To determine the alignment adjudication date 197B (at block 225), the system 100 determines the adjudication window buffer 193B (at block 220), which may be a constant, stored in the system 100, or may be variable depending upon, for example, the method used to deliver the prescribed medications to the customer. In any event, system 100 adds the adjudication window buffer 193B to the latest adjudication date to find the alignment adjudication date 197B. The adjudication window buffer 193B depicted in FIG. 6 ("Adjudication Window Buffer") is four days, making the alignment adjudication date 197B in FIG. 6 ("Alignment Adjudication Date") July 14.

The alignment processing buffer 193A represents the time it takes to adjudicate, fill, ship and deliver the aligned prescriptions A and B. Like the adjudication window buffer 193B, determining the alignment processing buffer 193A (at block 230) typically requires looking up the value in the database 182 or the database 146. In the example depicted in FIG. 6, the alignment processing buffer 193A, depicted as the period "Alignment Processing Buffer," is five days. The system 100 adds the combined total of the alignment processing buffer 193A and the patient start buffer 193D (one day in this example) to the alignment adjudication date 197B to determine the final alignment date 197C (at block 235). The final alignment date 197C depicted in FIG. 6 ("Alignment Date") is July 20. Of course, the adjudication processing buffer 193A may be any number, depending on the needs and/or circumstances of the system (e.g., how the prescription is delivered to the customer, etc.) or could be calculated for each prescription depending on various parameters (e.g., medication lead times, medication back-order status, warehousing considerations, shipping options selected, etc.). Moreover, the system may use a patient start buffer 193D that is more than one day and the term "day" as used herein may refer to business days or all days, depending on the particular embodiment of the system 100.

Once the system 100 determines the final alignment date 197C (at block 235), the system 100 can determine the parameters of any necessary short fills (at block 240) using the method 400. For each of the prescriptions A and B, the system 100 determines whether a short fill is necessary in order for the customer to have sufficient medication to reach the final alignment date 197C without missing any doses (at block 405). In the example illustrated in FIG. 6, the prescriptions A and B have remaining day supplies 196L of six days and nine days, respectively, and the final alignment date 197C ("Alignment Date") is 13 days from the current date. Thus, short fills are necessary for both of prescriptions A and B.

The system 100 proceeds to calculate the short-fill day-supply 198D (at block 410) for each of the prescriptions A and B. The system 100 determines short-fill day supply 198D, indicated in FIG. 6 ("RX A/B S/F Day Supply"), by calculating the number of days between the current date and the final alignment date 197C, and subtracting the remaining day supply 196L. FIG. 6 illustrates that the short-fill day-supply 198D for prescription A is four days (July 15-19), and that the short-fill day-supply 198D for prescription B is seven days (July 12-19).

The system 100 determines, for each required short fill, whether a short fill is possible and, if so, the short-fill delivery method 198H and short-fill delivery date 198F for the prescription (block 415). The example depicted in FIG. 6 assumes that the customer's preferred delivery method 195G is shipping the prescribed medication directly to the customer and that it is possible to deliver short fills for both Prescription A and Prescription B to the customer using that method (block 420). An estimated short-fill delivery date 198F for each of the short fills is determined (at block 440A) by incrementing the next adjudication date 196K for the prescription by the short fill processing buffer 193C for the prescription (e.g., by five days). The short-fill delivery dates 198F are July 15 and July 12, respectively, for the short fills of prescriptions A and B, as indicated by the timeline in FIG. 6 ("RX A/B S/F Delivery"). The current date plus the number of days indicated by the remaining day supply 196L is later than the short-fill delivery date 198F (block 445A), so the system 100 proceeds to calculate a short-fill quantity 198E for each of the prescriptions (block 470). The system 100 determines the short-fill quantity 198E for each of the prescriptions A and B by multiplying the short-fill day-supply 198D by the number of pills per day (the dose 196C). The system 100 saves the short fill parameters 198B-198H and final alignment date 197C (at block 250) because none of the prescription records 198 include an indication 198G that the short fill for the prescription is not possible (block 245). The prescriptions A and B would be filled according to the short fill parameters 198B-198H and the final alignment date 197C, and as depicted in FIG. 6.

Although the preceding text sets forth a detailed description of numerous embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the following claims.

What is claimed:

1. A method for aligning refill dates associated with a plurality of prescriptions for a customer to a single alignment date, each prescription for a medication, the method embodied in a set of machine-readable instructions executed on a processor and stored on a tangible medium, the method comprising:
   receiving a selection of a plurality of prescriptions to align;
   determining, for each of the plurality of selected prescriptions, a remaining day supply, the remaining day supply indicative of a number of days of the medication the customer has remaining;
   calculating a next adjudication date for each of the plurality of selected prescriptions;
   selecting as a latest adjudication date, from the plurality of calculated next adjudication dates, the next adjudication date occurring on the latest date;
   calculating an alignment adjudication date;
   calculating a final alignment date;
   wherein the final alignment date is different from at least one of the refill dates associated with one of the plurality of prescriptions for the customer
   determining via the processor, for each of the plurality of selected prescriptions, whether a short fill is required so that the customer does not exhaust the remaining day supply of the medication before the final alignment date;
   calculating via the processor a short-fill day supply for any prescription requiring a short fill;
   determining via the processor a date by which the customer will receive the short fill for any prescription requiring a short fill;
   determining via the processor, for any prescription requiring a short fill, whether the customer will exhaust the remaining day supply of the medication before the date by which the customer will receive the short fill for the prescription;

calculating via the processor a short-fill quantity for any prescription for which the customer will receive the required short fill for the prescription prior to exhausting the remaining day supply of the medication;

marking any prescription for which a short fill is required, but for which the short fill is not possible;

performing the following if one or more prescriptions are marked:
(i) recalculating via the processor the next adjudication date for each of the plurality of selected prescriptions;
(ii) selecting via the processor as the latest adjudication date, from the plurality of recalculated next adjudication dates, the next adjudication date occurring on the latest date;
(iii) recalculating via the processor the alignment adjudication date;
(iv) recalculating via the processor the final alignment date;
(v) determining via the processor for each of the plurality of selected prescriptions, using the recalculated dates, whether a short fill is required so that the customer does not exhaust the remaining day supply of the medication before the recalculated final alignment date;
(vi) recalculating via the processor the short-fill day supply for any prescription requiring a short fill;
(vii) adjudicating via the processor each of the selected prescriptions on or after the recalculated alignment adjudication date;
(viii) filling each of the selected prescriptions; and
(ix) providing each of the medications corresponding to the selected prescriptions to the customer by the recalculated final alignment date; and performing the following for each of the selected prescriptions if none of the prescriptions are marked;
(a) filling and providing to the customer the short-fill quantity for any prescription requiring a short fill;
(b) adjudicating via the processor each of the selected prescriptions on or after the alignment adjudication date;
(c) filling each of the selected prescriptions; and
(d) providing each of the medications corresponding to the selected prescriptions to the customer by the final alignment date.

2. The method of claim 1, wherein calculating a final alignment date further comprises adding one or more days to the alignment adjudication date for processing the prescriptions and providing the medications to the customer.

3. The method of claim 1, wherein calculating a next adjudication date further comprises determining via the processor a number of days corresponding to a percentage of a prescribed day supply for the medication.

4. The method of claim 1, wherein determining a date by which the customer will receive the short fill for any prescription requiring a short fill further comprises adding one or more days to the next adjudication date for the prescription for processing the prescription and providing the medication to the customer.

5. The method of claim 1, wherein the prescription is provided to the customer by a shipping service or a postal service and further comprising:
performing the following for any prescription for which the customer will not receive the short fill for the prescription prior to exhausting the remaining day supply of the medication:
(a) requesting the customer to pick up the short fill of the prescription from a retail location;
(b) indicating retail pickup of the short fill of the prescription if the customer agrees to retail pickup; and
(c) recalculating the short-fill day supply if the customer does not agree to retail pickup.

6. The method of claim 1, wherein providing each of the medications to the customer comprises providing the medications to the customer by a shipping service or a postal service.

7. The method of claim 1, wherein providing to the customer the short fill quantity for any prescription requiring a short fill further comprises:
providing the short fill to the customer by a preferred delivery method when, using the preferred delivery method, the customer will receive the short fill before exhausting the remaining day supply of the medication; and
evaluating an alternate delivery method when using the preferred delivery method would result in the customer exhausting the remaining day supply of the medication before receiving the short fill.

8. The method of claim 1, wherein short fills are not adjudicated.

9. The method of claim 1, wherein the customer comprises two or more people.

10. The method of claim 9, wherein the two or more people comprising the customer are members of the same family or are members of the same household.

11. A method for aligning refill dates associated with a plurality of prescriptions for a customer to a single alignment date, each prescription for a medication, the method embodied in a set of machine-readable instructions executed on a processor and stored on a tangible medium, the method comprising:
receiving a selection of a plurality of prescriptions to align;
determining, for each of the plurality of selected prescriptions, a remaining day supply, the remaining day supply indicative of how many days of the medication the customer has remaining;
calculating a final alignment date, wherein the final alignment date is different from at least one of the refill dates associated with one of the plurality of prescriptions for the customer;
determining via the processor, for each of the plurality of selected prescriptions, whether a short fill is required so that the customer does not exhaust the remaining day supply of the medication before the final alignment date;
calculating via the processor one or both of a short-fill day supply and a short-fill quantity for any prescription requiring a short fill;
filling and providing to the customer any required short fill, based on either the short-fill quantity or the short-fill day supply for the prescription; and
filling each of the selected prescriptions.

12. The method of claim 11, further comprising providing to the customer by the final alignment date each of the medications corresponding to the selected prescriptions.

13. The method of claim 11, wherein calculating a final alignment date further comprises complying with at least one adjudication rule set by a third-party payor.

14. The method of claim 13, wherein complying with at least one rule set by the third-party payor further comprises:
calculating via the processor, for each of the plurality of selected prescriptions, a next adjudication date;
selecting via the processor as a latest adjudication date, from the plurality of next adjudication dates, the next adjudication date occurring on the latest date;
calculating an alignment adjudication date; and selecting the final alignment date using the alignment adjudication date.

15. The method of claim 14, wherein selecting the final alignment date using the alignment adjudication date further comprises adding via the processor one or more days to the alignment adjudication date for processing the prescriptions and providing the medications to the customer.

16. The method of claim 14, wherein selecting the final alignment date using the alignment adjudication date further comprises adding via the processor one or more days to the alignment adjudication date as a patient start buffer.

17. The method of claim 14, wherein calculating, for each of the plurality of selected prescriptions, a next adjudication date, further comprises determining via the processor a number of days corresponding to a percentage of a prescribed day supply for the medication.

18. The method of claim 11, further comprising:
   determining, for any prescription requiring a short fill, a date by which the customer will receive the short fill; and
   wherein the date by which the customer will receive a short fill for a particular prescription is used to calculate one or both of the short-fill quantity and the short-fill day supply of medication corresponding to the particular prescription if the customer will receive the short fill for the particular prescription before exhausting the remaining day supply of the medication.

19. The method of claim 18, wherein medications are provided to the customer by a method involving lead time, and further wherein filling and providing to the customer any prescription requiring a short fill, based on the short-fill quantity or the short-fill day supply for the prescription, further comprises:
   determining, for any prescription requiring a short fill, whether the customer will receive the short fill for the prescription before the customer exhausts the remaining day supply of the medication corresponding to the prescription;
   performing the following for any prescription for which the customer will not receive the short fill for the prescription before the customer exhausts the remaining day supply of the medication corresponding to the prescription:
      (a) requesting the customer to pick up the short fill of the prescription from a retail location;
      (b) marking the short fill of the prescription for retail pickup if the customer agrees to retail pickup; and
      (c) recalculating one or both of the short-fill quantity and the short-fill day supply if the customer does not agree to retail pickup;
   determining whether any prescriptions are marked; and
   performing the following if one or more prescriptions are marked and the retail location cannot provide a short fill for each of the one or more marked prescriptions:
      (i) updating the next adjudication date for each of the selected prescriptions;
      (ii) recalculating the final alignment date;
      (iii) determining for each of the plurality of selected prescriptions, using the recalculated dates, whether a short fill is required so that the customer does not exhaust the remaining day supply of the medication before the recalculated final alignment date; and
      (iv) recalculating one or both of the short-fill day supply and the short-fill quantity for any prescription requiring a short fill.

20. The method of claim 18, wherein medications are provided to the customer by a first method involving lead time, and further wherein filling and providing to the customer any prescription requiring a short fill, based on the short-fill quantity or the short-fill day supply for the prescription, further comprises:
   determining, for any prescription requiring a short fill, whether the customer will receive the short fill for the prescription before the customer exhausts the remaining day supply of the medication corresponding to the prescription; and
   evaluating an alternate method for providing the medications to the customer if using the first method involving lead time will result in the customer exhausting the remaining day supply of the medication corresponding to the prescription before receiving the short fill for the prescription.

21. The method of claim 18, wherein determining, for any prescription requiring a short fill, a date by which the customer will receive the short fill, further comprises adding one or more days to the next adjudication date for the prescription for processing the prescription and providing the medication to the customer.

22. The method of claim 18, further comprising:
   marking any prescription for which a short fill is required, but for which the customer cannot receive the required short fill before exhausting the remaining day supply of the medication;
   performing the following if one or more prescriptions are marked:
      (i) updating the next adjudication date for each of the selected prescriptions;
      (ii) recalculating the final alignment date;
      (iii) determining for each of the plurality of selected prescriptions, using the recalculated dates, whether a short fill is required so that the customer does not exhaust the remaining day supply of the medication before the recalculated final alignment date; and
      (iv) recalculating the short-fill day supply or the short-fill quantity for any prescription requiring a short fill.

23. The method of claim 18, wherein prescriptions are provided to the customer by a method involving lead time, and further wherein filling and providing to the customer any required short fill, based on either the short-fill quantity or the short-fill day supply for the prescription, further comprises:
   determining, for any prescription requiring a short fill, whether the customer will receive the short fill for the prescription before the customer exhausts the remaining day supply of the medication;
   performing the following for any prescription for which the customer will not receive the short fill for the prescription before the customer exhausts the remaining day supply of the medication:
      (a) requesting the customer to pick up the short fill of the prescription from a retail location;
      (b) marking the short fill of the prescription for retail pickup if the customer agrees to retail pickup; and
      (c) recalculating one or both of the short-fill day supply and the short-fill quantity if the customer does not agree to retail pickup; and
   determining whether any prescriptions are marked; and
   wherein filling and providing to the customer any required short fill, based on the short-fill quantity or the short-fill day supply for the prescription, comprises delivering to the customer at a retail location the medications corresponding to any prescriptions marked for retail pickup.

24. The method of claim 18, further comprising:
   determining, for each required short fill, whether the short fill is possible using a preferred delivery method;

determining, for each required short fill that is possible by the preferred delivery method, whether the customer will receive the short fill before exhausting the remaining day supply of the medication;

determining, for each required short fill that is not possible using the preferred delivery method and for each required short fill that is possible using the preferred delivery method but for which the customer will not receive the short fill before exhausting the remaining day supply of the medication, whether the short fill is possible using an alternate delivery method;

marking the short fill as not possible if the short fill is not possible using the alternate delivery method or if the customer does not want to use the alternate delivery method; and determining, for each required short fill that is possible by the alternate delivery method and for which the customer wants to use the alternate delivery method, whether the customer will receive the short fill before exhausting the remaining day supply of the medication.

25. The method of claim 11, wherein filling and providing to the customer any required short fill comprises selecting one or more of the required short fills and providing the selected one or more short fills to the customer without adjudicating the selected short fills.

26. The method of claim 25, wherein the one or more selected short fills are selected because adjudicating the one or more selected short fills would delay the final alignment date.

27. The method of claim 11, wherein short fills are not adjudicated.

28. The method of claim 11, wherein the customer comprises two or more people.

29. The method of claim 28, wherein the two or more people comprising the customer are members of the same family or are members of the same household.

30. A system for aligning refill dates associated with a plurality of prescriptions for a customer to a single alignment date, each prescription for a medication, the system comprising:
- a network;
- a computer coupled to the network;
- a database coupled to the computer; and
- an alignment engine configured to run on the computer to determine parameters associated with the alignment of the plurality of prescriptions, the alignment engine configured to:
  - receive a selection of a plurality of prescriptions to align;
  - calculate a final alignment date, wherein the final alignment date is different from at least one refill date associated with one of the plurality of prescriptions for the customer; and
  - calculate a short-fill parameter.

31. The system of claim 30, wherein the alignment engine is further configured to determine a latest adjudication date, from a plurality of calculated next adjudication dates, in compliance with a rule determined by a third-party payor or a regulatory agency.

32. The system of claim 30, wherein the alignment engine is further configured to:
- retrieve information from the database; and
- calculate a parameter required to determine compliance with the rule determined by the third-party payor or the regulatory agency.

33. The system of claim 32, wherein the rule comprises an adjudication rule and wherein calculating a parameter required to determine compliance with the rule comprises calculating a percent-consumption period.

34. The system of claim 32, wherein calculating a short-fill parameter comprises one of the group consisting of:
- calculating a short-fill day supply;
- calculating a short-fill quantity; and
- calculating a short-fill delivery date.

35. A method for aligning refill dates associated with a plurality of prescriptions for a customer to a single alignment date, each prescription for a medication, the method embodied in a set of machine-readable instructions executed on a processor and stored on a tangible medium, the method comprising:
- receiving a selection of a plurality of prescriptions to align;
- determining via the processor, for each of the plurality of selected prescriptions, a remaining day supply, the remaining day supply indicative of how many days of the medication the customer has remaining;
- calculating via the processor a final alignment date, wherein the final alignment date is different from at least one of the refill dates associated with one of the plurality of prescriptions for the customer;
- determining via the processor, for each of the plurality of selected prescriptions, whether the customer will exhaust the remaining day supply of the medication before the final alignment date;
- filling and providing one intermediate fill of the medication for each of the selected prescriptions for which the customer will exhaust the remaining day supply of the medication before the alignment date; and
- filling each of the selected prescriptions.

36. The method of claim 35, wherein, for each medication for which one intermediate fill is provided, the one intermediate fill may be a short fill, a full fill, or an overfill.

* * * * *